US012721831B2

(12) United States Patent
DuBourdieu et al.

(10) Patent No.: US 12,721,831 B2
(45) Date of Patent: Sep. 1, 2026

(54) TETRAHYDROCURCUMINOID-METAL COMPLEXES, MANUFACTURING METHODS THEREOF, AND USES THEREOF

(71) Applicant: Probioticsmart, LLC, Menomonie, WI (US)

(72) Inventors: Daniel J. DuBourdieu, Limerick, ME (US); Rajiv Lall, Menomonie, WI (US)

(73) Assignee: Probioticsmart, LLC, Menomonie, WI (US)

(*) Notice: Subject to any disclaimer, the term of this patent is extended or adjusted under 35 U.S.C. 154(b) by 293 days.

(21) Appl. No.: 18/654,403

(22) Filed: May 3, 2024

(65) Prior Publication Data

US 2024/0325337 A1 Oct. 3, 2024

Related U.S. Application Data

(63) Continuation of application No. 17/319,496, filed on May 13, 2021, now abandoned.

(60) Provisional application No. 63/119,719, filed on Dec. 1, 2020, provisional application No. 63/024,904, filed on May 14, 2020.

(51) Int. Cl.

| | |
|---|---|
| ***A61K 31/315*** | (2006.01) |
| ***A23K 10/16*** | (2016.01) |
| ***A23K 20/111*** | (2016.01) |
| ***A23K 20/20*** | (2016.01) |
| ***A23K 50/75*** | (2016.01) |
| ***A23L 33/00*** | (2016.01) |
| ***A23L 33/105*** | (2016.01) |
| ***A23L 33/16*** | (2016.01) |
| ***A61K 31/192*** | (2006.01) |
| ***A61K 31/198*** | (2006.01) |
| ***A61K 31/353*** | (2006.01) |
| ***A61K 31/385*** | (2006.01) |
| ***A61K 31/7008*** | (2006.01) |
| ***A61K 31/716*** | (2006.01) |
| ***A61K 33/04*** | (2006.01) |
| ***A61K 35/748*** | (2015.01) |
| ***A61P 3/02*** | (2006.01) |
| ***A61P 37/06*** | (2006.01) |
| ***A61P 39/06*** | (2006.01) |
| ***C07F 3/06*** | (2006.01) |

(52) U.S. Cl.

CPC ............ *A61K 31/315* (2013.01); *A23K 10/16* (2016.05); *A23K 20/111* (2016.05); *A23K 20/30* (2016.05); *A23K 50/75* (2016.05); *A23L 33/105* (2016.08); *A23L 33/16* (2016.08); *A23L 33/40* (2016.08); *A61K 31/192* (2013.01); *A61K 31/198* (2013.01); *A61K 31/353* (2013.01); *A61K 31/385* (2013.01); *A61K 31/7008* (2013.01); *A61K 31/716* (2013.01); *A61K 33/04* (2013.01); *A61K 35/748* (2013.01); *A61P 3/02* (2018.01); *A61P 37/06* (2018.01); *A61P 39/06* (2018.01); *C07F 3/06* (2013.01); *A23V 2002/00* (2013.01)

(58) Field of Classification Search
None
See application file for complete search history.

(56) References Cited

U.S. PATENT DOCUMENTS

2021/0230090 A1* 7/2021 Ramirez Rios .......... A61K 8/11

FOREIGN PATENT DOCUMENTS

WO WO 2019008002 A1 1/2019

OTHER PUBLICATIONS

Aggarwal B.B., Deb L. and Prasad S. Curcumin Differs from Tetrahydrocurcumin for Molecular Targets, Signaling Pathways and Cellular Responses. Molecules 2015, 20, 185-205.

Casi "Tetrahydrocurcumin: The ultimate metabolite of curcuminoids". Dec. 17, 2015.

Colombo Alessia et al. A Highly Luminescent Tetrahydrocurcumin Ir III Complex with Remarkable Photoactivated Anticancer Activity, Chemistry—A European Journal, vol. 25(33) (2019) p. 7948-7952.

Dai J, Gu L, Su Y, Wang Q, Zhao Y, Chen X, Deng H, Li W, Wang G, Li K. Inhibition of curcumin on influenza A virus infection and influenzal pneumonia via oxidative stress, TLR2/4, p38/JNK MAPK and NF-κB pathways. Int Immunopharmacol. Jan. 2018.

Fosmire, G J. "Zinc toxicity." *The American journal of clinical nutrition* vol. 51,2 (1990): 225-7.

Harris Thomas M. et al. Benzylation at the Terminal Methyl Group of Certain Unsymmetrical [beta]-Diketones Through One of Two Possible Intermediate Dicarbanions, Journal of the American Chemical Society, vol. 81(5) (1959) p. 1160-1164.

Hieu T.Q. and Thao D.T.T. Enhancing the Solubility of Curcumin Metal Complexes and Investigating Some of Their Biological Activities. Journal of Chemistry vol. 2019, Article ID 8082195, 8 pages.

International Search Report and Written Opinion for corresponding PCT Application PCT/US2021/032242 dated Sep. 1, 2021.

McCarty, Mark F, and James J DiNicolantonio. "Nutraceuticals have potential for boosting the type 1 interferon response to RNA viruses including influenza and coronavirus." Progress in cardiovascular diseases, S0033-0620(20)30037-2. Feb. 12, 2020.

(Continued)

*Primary Examiner* — Danah Al-Awadi

(74) *Attorney, Agent, or Firm* — Daniel A. Blasiole; DeWitt LLP

(57) ABSTRACT

The invention is directed to tetrahydrocurcuminoid-metal complexes. The complexes can be included in compositions that further include additional nutraceutical antimicrobials, antioxidants, and immune boosters. The tetrahydrocurcuminoid-metal complexes can be administered to animals to increase animal health, reduce stress, reduce oxidative stress, maintain health, improve health, improve immunity, improve vaccination efficacy, increase feed conversion rate, decrease pro-inflammatory cytokine levels, or any combination thereof in an animal. The tetrahydrocurcuminoid-metal complexes of the invention exhibit enhanced bioavailability relative to the individual, non-complexed components.

18 Claims, 27 Drawing Sheets

(56) References Cited

OTHER PUBLICATIONS

Meza-Morales William et al. A New Family of Homoleptic Copper Complexes of Curcuminoids: Synthesis, Charcterization and Biological Properties, Molecules, vol. 24(5) (2019) p. 910.
Ostrowski W. , Uniecikowska L., Hoffmann M. , and Franski R. Demethoxycurcumin-Metal Complexes: Fragmentation and Comparison with Curcumin-Metal Complexes, as Studied by ESI-MS/MS Journal of Spectroscopy. vol. 2013, Article ID 749641, 8 pages.
Prasad, Sahdeo et al. "Metal-Curcumin Complexes in Therapeutics: An Approach to Enhance Pharmacological Effects of Curcumin." *International journal of molecular sciences* vol. 22,13 7094. Jun. 30, 2021.
Sangartit et al. "Tetrahydrocurcumin Protects against Cadmium induced Hypertension, Raised Arterial Stiffness and Vascular Remodeling in Mice" Dec. 11, 2014.
Shoba G, Joy D, Joseph T, Majeed M, Rajendran R, Srinivas PS. . Influence of piperine on the pharmacokinetics of curcumin in animals and human volunteers. Planta Med. May 1998;64(4):353-6.

* cited by examiner

Tetrahydrocurcumin Metal Curcumin Complex
(Metal could be - Zinc, Copper, Iron or others)

TETRAHYDROCURCUMINOID-METAL COMPLEXES, MANUFACTURING METHODS THEREOF, AND USES THEREOF

FIELD OF THE INVENTION

The present invention is directed to tetrahydrocurcuminoid-metal complexes and uses of same for maintaining and improving health and/or boosting immunity in animals.

BACKGROUND

Many health issues can be improved by supporting and having a healthy immune system. On the whole, the immune system does a remarkable job of defending against disease-causing microorganisms and other sources of stress on the immune system. Bacteria and flu viruses are sources of disease but less obvious sources of stress on the immune system include simply being old, or traveling or having emotional issues can be also be a source of stress. As good as the immune system is, it sometimes fails, a germ invades successfully, and sickness occurs. An underlying aspect to how all these sources of stress affect the body is oxidative stress from reactive oxygen species. Various infective agents can cause the production of free radicals and oxidative stress that, in turn, causes problems for cells, and this damage can spread throughout the body. For example, oxygen free radicals can react with cellular components to damage cells membranes, proteins, and DNA. Antioxidants combat the free radicals by donating an electron to the free radical of reactive oxygen species. Antioxidants are molecules that prevent free radicals from taking electrons and causing cellular damage. Antioxidants are able to give an electron to a free radical without becoming destabilized themselves because they are inherently stable without having a complete electron valence shell. As such, antioxidants can stop free radical chain reactions and limit the damage to the body. The body has some inherent antioxidants such as glutathione, but obtaining antioxidants from the diet or supplements can help reduce oxidative stress and help the immune system. Once the balance between the accumulation of reactive oxidative species and the removal of oxides is broken, oxidative stress is established. The ultimate consequences of this oxidative stress include tissue damage, inflammation responses, and cell death.

A strategy to improve general health would be to help reduce oxidative stress and also help the immune system in other more specific ways. The challenge is then to find antioxidants that can also boost the immune system.

SUMMARY OF THE INVENTION

The invention is directed in part to tetrahydrocurcuminoid-metal complexes. The tetrahydrocurcuminoid-metal complexes are complexes comprising at least one tetrahydrocurcuminoid chelated to a metal. The tetrahydrocurcuminoid-metal complexes of the invention encompass tetrahydrocurcuminoid-metal-tetrahydrocurcuminoid complexes and tetrahydrocurcuminoid-metal-curcuminoid complexes. The metal can be zinc or other metals. The molecular complex can be combined with additional interferon boosting nutraceuticals, such as *Spirulina* extracts, lipoic acid, ferulic acid, N-acetyl cysteine, or other nutraceuticals.

The tetrahydrocurcuminoid-metal complexes can be orally or topically delivered to animals for the purpose of stimulating the immune system in times of stress from diseases or other causes of stress to help maintain general health. Exemplary animals include mammals, fish, birds, and reptiles.

The invention helps animals achieve better overall health, especially in times of oxidative stress, such as from diseases or to maintain optimum immunity health on a daily basis. The tetrahydrocurcuminoid-metal complex compositions can be combined with other immune modulating agents to further enhance bioavailability and antioxidant capability to achieve optimal health.

The invention in some aspects encompasses a chelation of zinc or other metals to a tetrahydrocurcuminoid and a curcuminoid simultaneously.

The molecular complex of the invention further advances the art of stimulating the immune system by providing both tetrahydrocurcuminoids with curcuminoids orally or topically instead of relying on the body to metabolize curcuminoids into tetrahydrocurcuminoids, as tetrahydrocurcuminoids are not found in turmeric extracts. As certain curcuminoids and tetrahydrocurcuminoids have distinct benefits over one and another, the invention further advances the art by taking the advantages of both. The invention further advances the art by creating molecular tetrahydrocurcuminoid-metal-curcuminoid complexes that synergistically increase the antioxidant and immune stimulating capability of both tetrahydrocurcuminoids, such as tetrahydrocurcumin, and curcuminoids, such as curcumin. By having a synergistic capability, relatively less amount of the novel molecule of the invention is required to achieve the same efficacy for anti-oxidative, anti-inflammatory, and immune boosting aspects compared to the individual components of tetrahydrocurcuminoids, curcuminoids, and metals such as zinc. This allows for an even safer use of curcuminoids, tetrahydrocurcuminoids, and zinc and alleviates toxicity issues that might be possible when higher doses of these individual types of molecules have been used.

The objects and advantages of the invention will appear more fully from the following detailed description of the preferred embodiment of the invention made in conjunction with the accompanying drawings.

DETAILED DESCRIPTION OF THE INVENTION

Chelates

Figure 1:
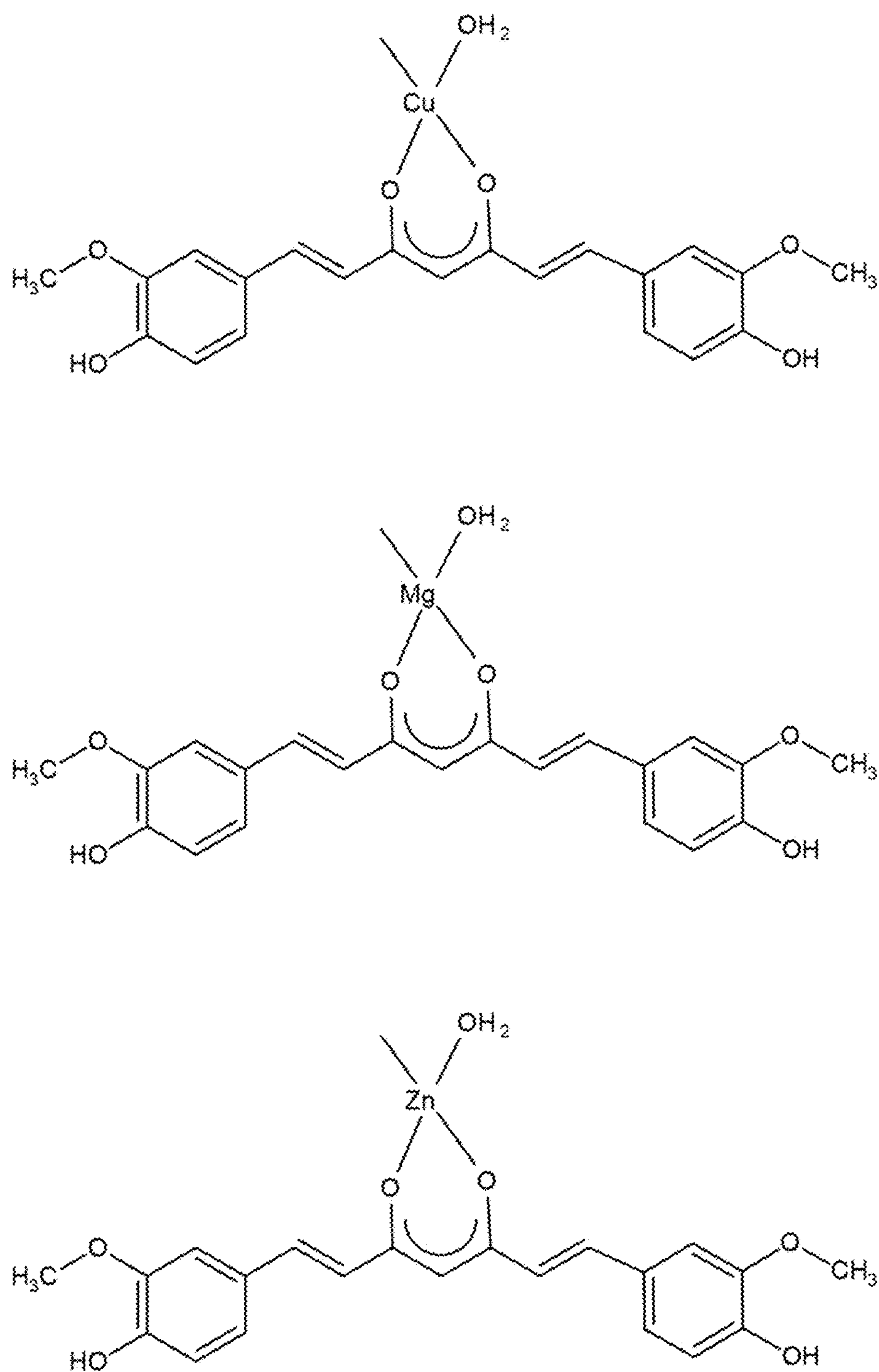
FIG. 1. Exemplary curcumin-metal complex structures.
Figure 2:
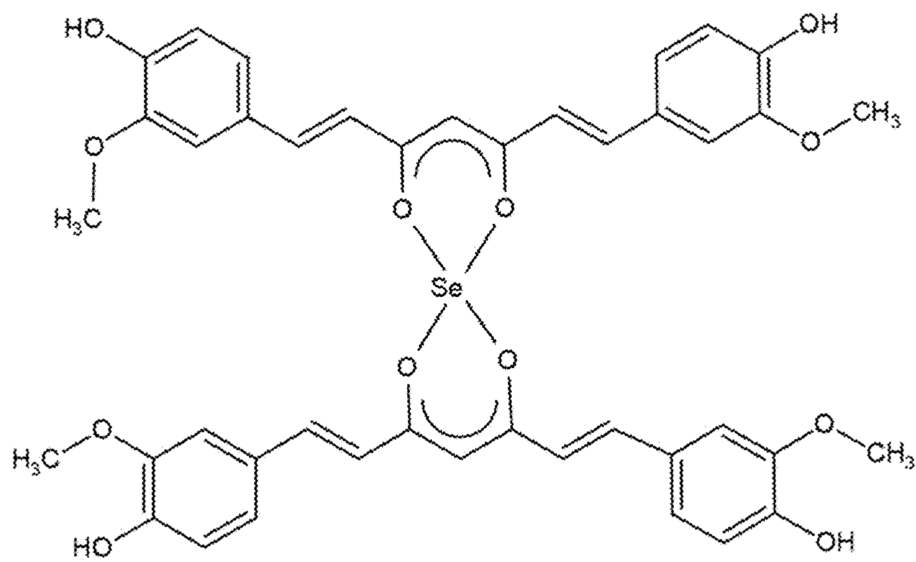
FIG. 2. Structure of an exemplary curcumin-metal-curcumin complex.
Figure 3:
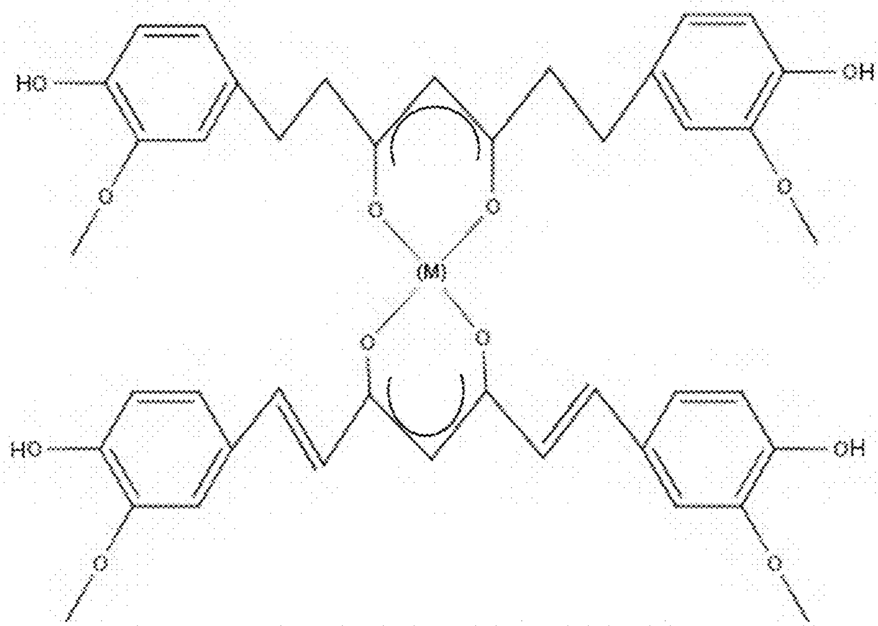
FIG. 3. Structure of an exemplary tetrahydrocurcumin-metal-curcumin complex of the invention.
Figure 4:
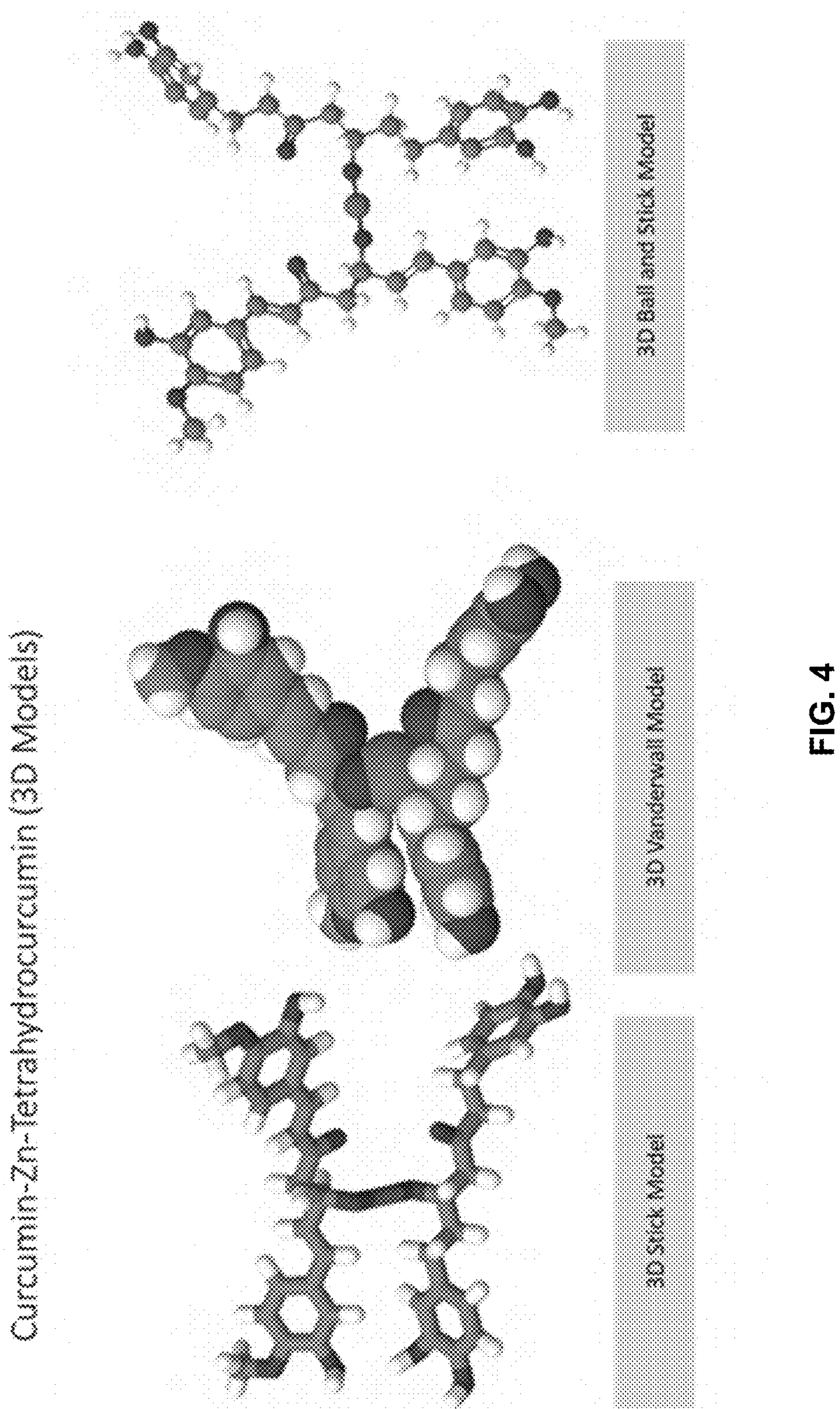
FIG. 4. 3D model structures of an exemplary tetrahydrocurcumin-metal-curcumin complex of the invention.

The invention in some aspects is directed to complexes comprising at least one tetrahydrocurcuminoid chelated to a metal (tetrahydrocurcuminoid-metal complexes). Chelation is a type of chemical bonding of ions and molecules to metal ions. It involves the formation or presence of two or more separate coordinate bonds between a polydentate (multiple bonded) ligand and a single central atom. The ionic form of the central atom can be critical to the success of chelation to the ligand, as divalent ions and trivalent ions do not always bind in the same manner. Various zinc forms can be utilized in the invention including zinc chloride, zinc acetate, zinc gluconate, zinc sulfate, zinc picolinate in anhydrous or hydrated formats. Other ionic metals can be used including iron, copper, cadmium, and iridium in the chelation bonding mechanism.

Zinc

Certain metals have been found to boost the immune system. Zinc is one such metal of a divalent nature. Zinc is essential for multiple cellular functions including immunity. Zinc is essential for normal development and function of cell-mediating innate immunity, neutrophils, and natural killer cell. Beneficial therapeutic response of zinc supplementation has been observed in the diarrhea of children, chronic hepatitis C, shigellosis, leprosy, tuberculosis, pneumonia, acute lower respiratory tract infection, common cold, and leishmaniasis. Zinc supplementation has been shown to be effective in decreasing incidences of infections in the elderly and patients with sickle cell disease and in decreasing incidences of respiratory tract infections in children. Zinc supplementation has prevented blindness in 25% of the elderly individuals with dry type of macular disorder. Zinc supplementation has been shown to be effective in decreasing oxidative stress and pro-inflammatory cytokines such as TNF-a and IL-1b in elderly individuals and patients. Zinc supplementation has been successfully used as a therapeutic and preventive agent for many conditions.

Zinc is considered to be relatively nontoxic, particularly if taken orally. However, manifestations of overt toxicity symptoms (nausea, vomiting, epigastric pain, lethargy, and fatigue) will occur with extremely high zinc intakes. Even lower levels of zinc supplementation, closer in amount to the recommended daily allowance (RDA), have been suggested to interfere with the utilization of copper and iron and to adversely affect HDL cholesterol concentrations. Individuals using zinc supplements should be aware of the possible complications attendant to their use. (Fosmire). As such, it is desirable to get the benefits of zinc in as low a dose as possible.

Curcumin

Besides metals like zinc that help the immune system, various nutraceuticals have been used to reduce oxidative stress. While there are many antioxidants available, ones from natural sources are of interest from a general safety point of view, provided certain stability problems can be overcome. One such natural antioxidant that can be used is curcumin, from the turmeric plant (Curcumin longa). Turmeric has been widely used as a spice in Indian food for thousands of years and contains a variety of constituents including curcuminoids such as curcumin, demethoxycurcumin and bisdemethoxycurcumin. Curcumin is the most widely known of these curcuminoids and is a naturally occurring polyphenolic phytoconstituent, isolated from turmeric rhizomes with uses as natural yellow colorant along with its use a spice in food. Curcumin also has many health benefits ranging from its anti-inflammatory actions in joints as an oxidative stress reducer to its anti-viral actions. Curcumin and curcuminoids interfere with the activity of a protein in the viruses used to invade the host cells. By doing so, the curcumin and curcuminoids prevent replications of the virus. Curcumin can reduce viral replication by over 90 percent in laboratory cells infected with influenza varieties. Curcumin decreases viral replication in infected cells, but also seems to protect other cells from becoming infected. Curcumin can also boost beta interferon levels reduce oxidative stress during influenza (Dai).

However, there are practical problems associated with using curcumin for boosting the immune system. Curcumin is insoluble in water under acidic or neutral conditions. Curcumin is unstable by undergoing rapid hydrolytic degradiation in neutral or alkaline conditions. Since it is insoluble in aqueous medium and has poor stability towards oxidation, light, alkalinity, enzymes and heat, curcumin cannot really be widely used in pharmaceutical preparations unless stability issues can be overcome.

Turmeric and extracts with curcuminoids are considered safe when taken orally and when used topically by most people. Turmeric products that provide up to 8 grams of curcumin daily appear to be safe when used for up to 2 months (e.g., 0.05 g curcumin/lb. body weight). Turmeric typically does not cause serious side effects. Some people can experience mild side effects such as stomach upset, nausea, dizziness, or diarrhea. These side effects are more common at higher doses. However, under certain health conditions, curcumin can cause problems with people with gallbladder problems, bleeding problems where turmeric might slow blood clotting, in diabetes where curcumin might decrease blood sugar in diabetic people, after surgery where turmeric might slow blood clotting and other possible situations. As such, being able to use less curcumin to achieve its beneficial health effects rather than higher amounts of curcumin is desirable.

Curcumin is a ligand that forms stable complexes with certain metal ions and nonmetals. In general, stable structures with 1:1, 2:1 and 3:1 (ligand:metal) stoichiometry can occur. Complexation of curcumin with aluminum, copper, or iron has been used for the treatment of Alzheimer's disease and with zinc for increases in vitro antioxidant activity.

Tetrahydrocurcumin

When curcumin is ingested, it is metabolized by cells. One of the major metabolites of curcumin is tetrahydrocurcumin (THC), which lacks the α,β-unsaturated carbonyl moiety and is white in color whereas curcumin is a yellow color. Tetrahydrocurcumin is not found in turmeric plants and has to be metabolized from curcumin by the body. Curcumin and tetrahydrocurcumin exhibit different biological properties. Tetrahydrocurcumin exhibits higher antioxidant activity, whereas curcumin exhibits both pro-oxidant and antioxidant properties. Curcumin appears to bind to and modulate the activities of a wide variety of targets. Tetrahydrocurcumin, however, appears to be a superior antioxidant that lacks both anti-inflammatory and pro-oxidant activities. (Aggarwal). Tetrahydrocurcumin is superior to curcumin for induction of glutathione peroxidase, glutathione-S-transferase, and NADPH: quinone reductase, and the quenching of free radicals. It is possible that curcumin and tetrahydrocurcumin are taken up and metabolized differently in cells, which thus determines their biological activity. However, curcumin offers antiviral capability against the flu. Therefore, if possible, one should use both curcumin and tetrahydrocurcumin to boost the immune system to get advantages of both. However, like curcumin, tetrahydrocurcumin also is not very water soluble. This makes both curcumin and tetrahydrocurcumin poorly bioavailable and problematic for practical uses in readily boosting the immune system in supplements. As such, there is a need to develop methods to increase tetrahydrocurcumin bioavailability and stability.

The complexation metals to tetrahydrocurcumin has not been explored in any detail for increasing stability, bioavailability, and for boosting the immune system and thus represents a novel solution to these problems. The concurrent complexation of both tetrahydrocurcumin and curcumin to metals has also not been carried out previously. Complexing a metal such as zinc to tetrahydrocurcumin and to curcumin simultaneously therefore represents an advance in the state of the art for the formation of a novel molecular complex. Bonding both curcumin and tetrahydrocurcumin together through a metal bridge by chelation bonding allows for a synergistic increase in their representative efficacies for antioxidant capability and representative immune stimulating capability. This novel complex molecule solves the problems of stability and bioavailability of curcumin and tetrahydrocurcumin and further allows for a single molecule to have the health effects of both curcumin and tetrahydrocurcumin to synergistically occur efficiently.

Other Nutraceuticals to Help the Immune System

When viruses infect cells, one of the immune system's responses is to create interferon that will, in turn, help eliminate viruses. Besides curcumin, certain other nutraceuticals can help boost type 1 interferon levels in the cell. Elderberry (*Sambucus*) extracts containing anthocyanins, ferulic acid, N-acetyl cysteine, *Spirulina* extracts, selenium, lipoic acid, yeast beta glucans, glucosamine are expected to boost induction of type 1 interferon (McCarty). As an adjunct, these nutraceuticals can complement the activities of the tetrahydrocurcuminoid-metal-curcuminoid complexes of the invention in boosting the immune system or maintaining optimum immunity on a daily basis.

Complex Components

As used herein, "tetrahydrocurcuminoid" refers to a compound having the structure:

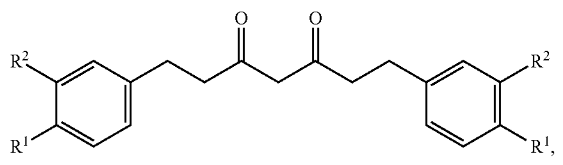

wherein each $R^1$ and $R^2$ are independently selected from the group consisting of H, OH, and $OCH_3$, and salts, esters, tautomers (e.g., enols), and chelates thereof. In some versions, each $R^1$ is independently selected from the group consisting of H and OH. In some versions, each $R^1$ is OH. In some versions, each $R^2$ is selected from the group consisting of H and $OCH_3$. In some versions, each $R^2$ is $OCH_3$. In some versions, each $R^2$ is H. In some versions, one $R^2$ is $OCH_3$, and one $R^2$ is H. Exemplary tetrahydrocurcuminoids include tetrahydrocurcumin, wherein each $R^1$ is OH, and each $R^2$ is $OCH_3$; tetrahydrodemethoxycurcumin, wherein each $R^1$ is OH, one $R^2$ is $OCH_3$, and one $R^2$ is H; and tetrahydrobisdemethoxycurcumin, wherein each $R^1$ is OH, and each $R^2$ is H.

As used herein, "curcuminoid" refers to a compound having the structure:

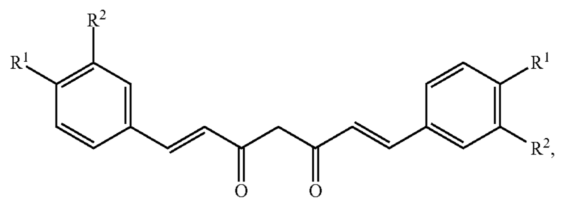

wherein each $R^1$ and $R^2$ are independently selected from the group consisting of H, OH, and $OCH_3$, and salts, esters, tautomers (e.g., enols), and chelates thereof. In some versions, each $R^1$ is independently selected from the group consisting of H and OH. In some versions, each $R^1$ is OH. In some versions, each $R^2$ is selected from the group consisting of H and $OCH_3$. In some versions, each $R^2$ is $OCH_3$. In some versions, each $R^2$ is H. In some versions, one $R^2$ is $OCH_3$, and one $R^2$ is H. Exemplary curcuminoids include curcumin, wherein each $R^1$ is OH, and each $R^2$ is $OCH_3$; demethoxycurcumin, wherein each $R^1$ is OH, one $R^2$ is $OCH_3$, and one $R^2$ is H; and bisdemethoxycurcumin, wherein each $R^1$ is OH, and each $R^2$ is H.

As used herein, "tetrahydrocurcuminoid-metal complex" refers to a complex comprising at least one tetrahydrocurcuminoid chelated to a metal. Some tetrahydrocurcuminoid-metal complexes of the invention include more than one tetrahydrocurcuminoid chelated to the metal. Some tetrahydrocurcuminoid-metal complexes of the invention include at least one tetrahydrocurcuminoid chelated to the metal in addition to another compound chelated to the metal. Exemplary tetrahydrocurcuminoid-metal complexes include tetrahydrocurcuminoid-metal-tetrahydrocurcuminoid complexes and tetrahydrocurcuminoid-metal-curcuminoid complexes.

As used herein, "tetrahydrocurcuminoid-metal-tetrahydrocurcuminoid complex" refers to a complex comprising at least two tetrahydrocurcuminoids chelated to a common metal.

As used herein, "tetrahydrocurcuminoid-metal-curcuminoid complex" refers to a complex comprising at least one tetrahydrocurcuminoid and at least one curcuminoid chelated to a common metal.

As used herein, "curcuminoid-metal-curcuminoid complex" refers to a complex comprising two curcuminoids chelated to a common metal.

The metal in the curcuminoid-metal-curcuminoid complexes, tetrahydrocurcuminoid-metal-tetrahydrocurcuminoid complexes, and tetrahydrocurcuminoid-metal-curcuminoid complexes can be a divalent metal or a trivalent metal. Exemplary suitable divalent metals include zinc, copper cadmium, and cobalt. Exemplary suitable trivalent metals include iron, ruthenium, iridium, and aluminum.

An exemplary structure of a tetrahydrocurcuminoid-metal-curcuminoid complex of the invention is:

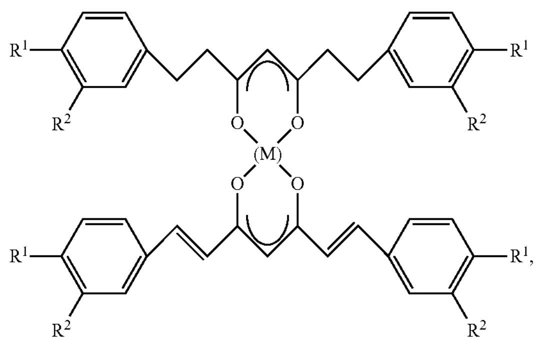

wherein each $R^1$ and $R^2$ are independently selected from the group consisting of H, OH, and $OCH_3$, and salts and esters thereof. In some versions, each $R^1$ is independently selected from the group consisting of H and OH. In some versions, each $R^1$ is OH. In some versions, each $R^2$ is selected from the group consisting of H and $OCH_3$. In some versions, each $R^2$ is $OCH_3$. In some versions, each $R^2$ is H. In some versions, one $R^2$ is $OCH_3$, and three $R^2$ are H. In some versions, two $R^2$ are $OCH_3$, and two $R^2$ are H. In some versions, three $R^2$ are $OCH_3$, and one $R^2$ is H.

Exemplary Methods of Generating Tetrahydrocurcuminoid-Metal Complexes

To generate the complexes of the invention, a first ligand (e.g., tetrahydrocurcuminoid) either alone or together with second ligand (e.g., curcuminoid) can be solubilized together or separately in a suitable solvent to generate solubilized ligand. In one example, 0.5 parts by number (e.g., 0.5 mole) of one or more tetrahydrocurcuminoids and 0.5 parts by number (e.g., 0.5 mole) of one or more curcuminoids can be solubilized together in an organic solvent such as methanol, ethanol, glycerol, propylene glycol, or other suitable solvent. This gives 1 part of (e.g., 1 mole) total tetrahydrocurcuminoid/curcuminoid ligand with each ligand in a 1:1 ratio by number. Other relative ratios of tetrahydrocurcuminoid:curcuminoid can be used depending on the requirements of the final product. Exemplary tetrahydrocurcuminoid:curcuminoid ratios (by number) include 100:1, 75:1, 50:1, 25:1, 10:1, 7:1, 3:1, 1:1, 1:3, 1:7, 1:10, 1:25, 1:50, 1:75, and 1:100, any ranges between these exemplary ratios, or any and ratios or ranges above or below these exemplary ratios.

One part of metal (e.g., zinc) by number (e.g., 1 mole) can then be solubilized in a suitable solvent such as water or organic solvent, depending on the format of the metal.

The solubilized metal can then be combined with the solubilized ligand, preferably in a 1:1 number ratio of metal:ligand, to generate a mixed solution. Other ratios of metal:ligand can be used. Exemplary metal:ligand ratios (by number) include 100:1, 75:1, 50:1, 25:1, 10:1, 7:1, 3:1, 1:1, 1:3, 1:7, 1:10, 1:25, 1:50, 1:75, and 1:100, any ranges between these exemplary ratios, or any and ratios or ranges above or below these exemplary ratios.

The mixed solution can optionally have its pH adjusted to a pH from about 6.5 to about 8.5. The pH adjustment can be performed with a reagent such as triethylamine, sodium hydroxide, potassium hydroxide, and/or sodium bicarbonate.

The combined metal and ligand in the mixed solution can be stirred at room temperature or higher for 2 hours or longer as required for complexation to occur.

The solvent can then be removed from the complexed composition by filtration or other means, washed in water as required to remove unreacted metal, and further dried to create a powder. Analysis of the complex can be carried to quantify the metal content of the complex. Ultraviolet (UV) and Fourier-transform infrared spectroscopy (FTIR) analysis methods can be used to determine that complexation has occurred by comparing to control ligand.

The powder can be mixed with other components, such anti-inflammatory agents, immune boosting agents, antioxidants, phytobotanicals, and/or carriers.

More generally, the methods of making the tetrahydrocurcuminoid-metal complexes of the invention can comprise: solubilizing one or more first compounds in a first solvent to form a first solution, wherein the one or more first compounds comprises a tetrahydrocurcuminoid; solubilizing a metal in a second solvent to form a second solution; mixing the first solution with the second solution to thereby form a mixed solution comprising the one or more first compounds, the metal, and a mixed solvent comprising the first and second solvents; and incubating the mixed solution for a time and a temperature suitable for generating the tetrahydrocurcuminoid-metal complex. In some versions, the one or more first compounds further comprises a curcuminoid. The methods can further comprise: solubilizing one or more third compounds in a third solvent to form a third solution, wherein the one or more third compounds comprises a curcuminoid; and mixing the third solution with the first solution and the second solution to thereby form the mixed solution, wherein the mixed solution comprises the one or more first compounds, the one or more second compounds, the metal, and the mixed solvent comprising the first, second, and third solvents. The methods can further comprise, after the incubating, removing the mixed solvent from the tetrahydrocurcuminoid-metal complex. The methods can further comprise, after the removing, drying the tetrahydrocurcuminoid-metal complex into a powder. The methods can further comprise, prior to or during the incubating, adjusting the pH of the mixed solution to a pH of from 6.5 to 8.5. In some versions, the adjusting comprises adding at least one of triethylamine, sodium hydroxide, potassium hydroxide, and sodium bicarbonate to the mixed solution. In some versions, the incubating is conducted at a pH from 6.5 to 8.5.

In some versions, the methods of making the tetrahydrocurcuminoid-metal complexes of the invention can comprise incubating one or more first compounds and a metal in a solvent for a time and a temperature suitable for generating the tetrahydrocurcuminoid-metal complex. In some versions, the one or more first compounds comprises a tetrahydrocurcuminoid. In some versions, the one or more first compounds further comprises a curcuminoid. The methods can further comprise, after the incubating, removing the mixed solvent from the tetrahydrocurcuminoid-metal complex. The methods can further comprise, after the removing, drying the tetrahydrocurcuminoid-metal complex into a powder. The methods can further comprise, prior to or during the incubating, adjusting the pH of the mixed solution to a pH of from 6.5 to 8.5. In some versions, the adjusting comprises adding at least one of triethylamine, sodium hydroxide, potassium hydroxide, and sodium bicarbonate to the mixed solution. In some versions, the incubating is conducted at a pH from 6.5 to 8.5. In some versions, the one or more first compounds and the metal are mixed in dry form prior to mixing with the solvent. In some versions, the one or more first compounds and the metal are each added separately in dry form to the solvent.

Compositions, Components Thereof, and Uses Thereof

The tetrahydrocurcuminoid-metal complexes of the invention can be included in a composition suitable for administration to an animal. The composition can be suitable for oral administration or topical administration. The compositions can be in a solid form, a liquid form, or a semi-solid form (e.g., gel, paste, cream). Exemplary solid forms include powder, tablets, etc.

The tetrahydrocurcuminoid-metal complexes can be included in the composition in an amount from 0.0000000001% w/w to 99.999999999% w/w. Exemplary amounts include 0.10% w/w, 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, or 95% w/w; any range between these amounts, or any amount or range above or below these amounts.

In some versions, the composition includes a combination of tetrahydrocurcuminoid-metal-curcuminoid complexes and tetrahydrocurcuminoid-metal-tetrahydrocurcuminoid complexes; tetrahydrocurcuminoid-metal-curcuminoid complexes and curcuminoid-metal-curcuminoid complexes; tetrahydrocurcuminoid-metal-tetrahydrocurcuminoid complexes and curcuminoid-metal-curcuminoid complexes; or tetrahydrocurcuminoid-metal-curcuminoid complexes, tetrahydrocurcuminoid-metal-tetrahydrocurcuminoid complexes, and curcuminoid-metal-curcuminoid complexes. The combination can be included in the composition in an amount from 0.0000000001% w/w to 99.999999999% w/w. Exemplary amounts include 0.1% w/w, 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, or 95% w/w; any range between these amounts, or any amount or range above or below these amounts.

The composition can include any of a number of additional components, such as inert carriers and/or active ingredients. Each additional component can be included in the composition in an amount from 0.0000000001% w/w to 99.999999999% w/w. Exemplary amounts include 0.1% w/w, 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, or 95% w/w; any range between these amounts, or any amount or range above or below these amounts. "Active ingredients" are ingredients other than the tetrahydrocurcuminoid-metal complexes of the invention having therapeutic or other value when administered to an animal, such as drugs, nutrients, cosmeceuticals, diagnostic agents, nutritional agents, and the like. Exemplary types of active ingredients include anti-inflammatory agents, antioxidants, antimicrobial agents, and immune boosters. Exemplary antioxidants include phytobotanicals, anthocyanins, polyphenols, ferulic acid, N-acetyl cysteine, *Spirulina* extracts, selenium, lipoic acid, yeast beta glucans, and glucosamine. Exemplary antimicrobial agents include phytobotanicals. Exemplary immune boosting agents include zinc and selenium. Exemplary inert carriers include water or other inert carriers known in the art.

The amounts of each of the components in the final product may be varied depending upon the nature of the additional components, the weight and condition of the animal to be treated, and the unit dosage desired. Those of ordinary skill in the art will be able to adjust dosage amounts as required.

Exemplary forms of the compositions of the invention include soft chews, powders, capsules, tablets, boluses, pastes, liquids, foods, animal feeds, candies, drinks, pastes, liquids, and creams. Exemplary composition forms suitable for oral administration include tablets, boluses, pastes, capsules, liquids, such as human foods, animal feeds, candy, soft chews, or drinks. Exemplary composition forms suitable for topical administration include pastes, liquids, gels, or creams.

The components of the invention can be placed into capsules, boluses, and tablets for oral administration or in pastes, liquids, gels, or creams for topical administration in times of oxidative stress from diseases or to maintain optimum immunity health on a daily basis. The components of the invention may also be placed into human foods and animal feeds including cereals, soups, liquid drinks, candy, pharmaceuticals aids including band aids, skin care beauty creams, and pastes.

Some versions of the invention include the tetrahydrocurcuminoid-metal complex in combination with any one or more, in any combination, of black elderberry (a phytonutrient supporting immune function and promoting a healthy respiratory system), selenium (a micronutrient that helps fight cellular damage), vitamin D3 (builds immunity in times of stress), vitamin C (ascorbic acid, an antioxidant for maintaining production of white blood cells), phycocyanin (a *Spirulina* extract that provides support by helping to maintain normal interferon levels during oxidative stress), ferulic acid (an organic compound with antioxidant properties that support the body during stress), and piperine (black pepper extract that helps the body by increasing bioavailability of nutraceuticals like curcumin). These components can be included in powder form. The components can be encapsulated in a capsule or provided in any other form provided herein.

The compositions can be used in methods of reducing stress, reducing oxidative stress, maintaining health, improving health, improving immunity, improving vaccination efficacy, increasing feed conversion rate, or decreasing pro-inflammatory cytokine levels in an animal in an animal (such as a mammal, human, poultry, etc.). The methods can comprise administering a composition of the invention to the animal in a therapeutically effective amount. The therapeutically effective amount can include an amount effective to reduce stress, reduce oxidative stress, maintain health, improve health, improve immunity, improve vaccination efficacy, increase feed conversion rate, or decrease pro-inflammatory cytokine levels in an animal.

The animal in some versions can include an animal suffering from any condition or disease described herein. Exemplary diseases include cancer, arthritis, inflammatory conditions, cardiovascular conditions, neurological conditions, pulmonary conditions, diabetes, hepatic conditions, gastrointestinal conditions, and an infectious disease, and other conditions that place stresses on the body. Exemplary cardiovascular conditions comprise coronary artery disease, stroke, heart failure, hypertensive heart disease, rheumatic heart disease, and cardiomyopathy, among others. Exemplary neurological conditions comprise diseases of the central and peripheral nervous system, including the brain, spinal cord, cranial nerves, peripheral nerves, nerve roots, autonomic nervous system, neuromuscular junction, and muscles. These conditions include epilepsy, Alzheimer disease and other dementias, cerebrovascular diseases including stroke, migraine and other headache disorders, multiple sclerosis, Parkinson's disease, neuroinfections, brain tumors, traumatic disorders of the nervous system due to head trauma, and neurological disorders as a result of malnutrition. Exemplary pulmonary conditions include asthma, chronic obstructive pulmonary disease (COPD), chronic bronchitis, emphysema, lung cancer, cystic fibrosis/bronchiectasis, pneumonia, pleural effusion, and COVID-19. Exemplary forms of diabetes include type 1 diabetes and type 2 diabetes. Exemplary hepatic conditions comprise hepatitis A infection, hepatitis B infection, and hepatitis C infection, fatty liver disease, cirrhosis, liver cancer, and inherited diseases such as hemochromatosis and Wilson disease. Exemplary gastrointestinal conditions comprise celiac disease, irritable bowel syndrome, and irritable bowel disease (Crohn's disease, ulcerative colitis). Exemplary infectious diseases include viral diseases, prion diseases, and bacterial diseases. The animal can include an animal to be or having been vaccinated within a period of 8 weeks, 7 weeks, 6 weeks, 5 weeks, 4 weeks, 3 weeks, 2 weeks, 1 week, 6 days, 5 days, 4 days, 3 days, 2 days, or 1 day. The therapeutically effective amount can be an amount effective to ameliorate the condition or disease or a symptom of the condition or disease.

The animal can comprise any animal. The animal can comprise a human or a non-human animal. The animal can comprise a mammal. Exemplary mammals include humans, bovines, swine, sheep, goats, dogs, cats, primates, apes, monkeys, and rodents. The animal can comprise a bird, such as poultry. The animal can comprise other types of animal, such as fish or reptiles. In some versions, the animal comprises a production animal. Production animals are animals that are farmed for food or products derived therefrom. Exemplary production animals include bovines (including cattle), ovines (including sheep), caprines (including goats), avines (including birds such as poultry), cervines (including deer), porcines (including pigs), reptilians (including reptiles), and piscines (including fish).

The compositions of the invention can be used as feed additive to help animals (such as production animals) gain weight faster. In some versions, the compositions can serve as an alternative to antibiotics intended for weight gain and growth promotion in production animals. The animal in such versions can comprise any production animal, such as bovines (including cattle), ovines (including sheep), caprines (including goats), avines (including birds such as poultry), cervines (including deer), porcines (including pigs), reptilians (including reptiles), piscines (including fish), or any other production animal. In some versions, the composition is administered in an amount effective to increase feed conversion rate in the animal relative to a control animal not receiving the composition.

In some versions, the composition is administered in an amount effective to decrease serum levels of a pro-inflammatory cytokine in the animal relative to a control animal not receiving the composition. Exemplary pro-inflammatory cytokines include IL-2, IL-8, IL-6, IL-7, IL-15, IL-18, MCP-1, TNF$\alpha$, and IL-1-beta.

Some versions of the invention comprise a mixture comprising free tetrahydrocurcuminoid (uncomplexed tetrahydrocurcuminoid) and free zinc (uncomplexed zinc) in the form of a dry powder. The free tetrahydrocurcuminoid can comprise tetrahydrocurcumin. The mixture can be made without the use of a solvent. The mixture can be administered to an animal directly in powder form or mixed with a carrier before administering. The mixture can also or alternatively be solubilized in a solvent as described herein to permit complexation of the tetrahydrocurcuminoid and the zinc. The tetrahydrocurcuminoid and the zinc can be present in the mixture in a ratio from 0.001:1 (tetrahydrocurcuminoid:zinc) to 1000:1 (tetrahydrocurcuminoid:zinc), such as a ratio from 0.01:1 (tetrahydrocurcuminoid:zinc) to 100:1 (tetrahydrocurcuminoid:zinc).

Some versions of the invention comprise a mixture comprising free tetrahydrocurcuminoid (uncomplexed tetrahydrocurcuminoid), free curcuminoid (uncomplexed curcuminoid), and free zinc (uncomplexed zinc) in the form of a dry powder. The free tetrahydrocurcuminoid can comprise tetrahydrocurcumin. The free curcuminoid can comprise curcumin. The mixture can be made without the use of a solvent. The mixture can be administered to an animal directly in powder form or mixed with a carrier before administering. The mixture can also or alternatively be solubilized in a solvent as described herein to permit complexation of the tetrahydrocurcuminoid, the curcuminoid, and the zinc. The tetrahydrocurcuminoid and the zinc can be present in the mixture in a ratio from 0.001:1 (tetrahydrocurcuminoid:zinc) to 1000:1 (tetrahydrocurcuminoid:zinc), such as a ratio from 0.01:1 (tetrahydrocurcuminoid:zinc) to 100:1 (tetrahydrocurcuminoid:zinc); the zinc and curcuminoid can be present in a ratio from 0.001:1 (zinc:curcuminoid) to 1000:1 (zinc:curcuminoid), such as a ratio from 0.01:1 (zinc:curcuminoid) to 100:1 (zinc:curcuminoid); and/or the tetrahydrocurcuminoid and curcuminoid can be present in a ratio from 0.001:1 (tetrahydrocurcuminoid:curcuminoid) to 1000:1 (tetrahydrocurcuminoid:curcuminoid), such as a ratio from 0.01:1 (tetrahydrocurcuminoid:curcuminoid) to 100:1 (tetrahydrocurcuminoid:curcuminoid).

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1

One mole of tetrahydrocurcumin was solvated in anhydrous ethanol and placed into a beaker. One mole of zinc chloride was solvated in anhydrous ethanol and placed into the same beaker. A stir bar was added, and the mixture was stirred for 2 hours at room temperature to create a tetrahydrocurcumin-zinc-tetrahydrocurcumin complex. The mixture was placed into a rotoevaporator flask, and the ethanol was removed. The tetrahydrocurcumin-zinc-tetrahydrocurcumin complex was placed into a Buchner funnel and thoroughly washed with water to remove unreacted components. The washed complex was dried at 50° C. until a dry powder was formed. The complex was analyzed for zinc content to quantify the amount of zinc in the complex. It was found that 23% of the starting zinc remained in the dried tetrahydrocurcumin powder, consistent with zinc being bound by chelation bonds to tetrahydrocurcumin.

Example 2

Two moles of tetrahydrocurcumin were solvated in anhydrous ethanol and placed into a beaker. One mole of zinc chloride was solvated in anhydrous ethanol and placed into the same beaker. A stir bar was added, and the mixture was stirred for 2 hours at room temperature to create a tetrahydrocurcumin-zinc-tetrahydrocurcumin complex. The mixture was placed into a rotoevaporator flask, and the ethanol was removed. The tetrahydrocurcumin-zinc-tetrahydrocurcumin complex was placed into a Buchner funnel and washed with water to remove unreacted components. The washed complex was dried at 50° C. until a dry powder was formed. The complex was analyzed for zinc content to quantify the amount of zinc in the complex.

Example 3

One mole of tetrahydrocurcumin was solvated in propylene glycol and placed into a beaker. One mole of zinc chloride was solvated in water and placed into the same beaker. The propylene glycol:water ratio was 1:1. A stir bar was added and the mixture was stirred for 2 hours at room temperature to create a tetrahydrocurcumin-zinc-tetrahydrocurcumin complex. The tetrahydrocurcumin-zinc-tetrahydrocurcumin complex was placed into a Buchner funnel and washed with water to remove unreacted components. The washed complex was dried at 50° C. until a dry powder was formed. The complex was analyzed for zinc content to quantify the amount of zinc in the complex.

Example 4

0.25 moles of tetrahydrocurcumin and 0.75 moles of curcumin were solvated in methanol to create 1 mole of ligand and placed in a beaker. One mole of zinc acetate anhydrous was solvated in methanol and added to the beaker to give a 1:1 molar ratio of ligand:metal. A stir bar was added, and the mixture was stirred for 2 hours at room temperature to create a tetrahydrocurcumin-zinc-curcumin complex. The mixture was placed into a rotary evaporator flask, and the methanol was removed. The tetrahydrocurcumin-zinc-curcumin complex was placed into a Buchner funnel and washed with water to remove unreacted components. The washed complex was dried at 50° C. until a dry powder was formed. The complex was analyzed for zinc content to quantify the amount of zinc in the complex. UV and FTIR analysis showed characteristic changes in profiles compared to the control material of methanol-solvated tetrahydrocurcumin and curcumin mixture.

Example 5

One mole of tetrahydrocurcumin and 1 mole of curcumin were solvated in methanol to create 2 moles of ligand and placed in a beaker. One mole of zinc acetate anhydrous was solvated in methanol and added to the beaker to give a 2:1 molar ratio of ligand:metal. A stir bar was added, and the mixture was stirred for 2 hours at room temperature to create a tetrahydrocurcumin-zinc-curcumin complex. The mixture was placed into a rotary evaporator flask, and the methanol was removed. The complex of tetrahydrocurcumin-zinc-curcumin was placed into a Buchner funnel and washed with water to remove unreacted components. The washed complex was dried at 50° C. until a dry powder was formed. The complex was analyzed for zinc content to quantify the amount of zinc in the complex. UV and FTIR analysis showed characteristic changes in profiles compared to the control material of methanol-solvated tetrahydrocurcumin and curcumin mixture.

Example 6

One mole of tetrahydrocurcumin and 1 mole of curcumin were solvated in methanol to create 2 moles of ligand and placed in a beaker. One mole of zinc chloride was solvated in methanol and added to the beaker to give a 2:1 molar ratio of ligand:metal. A stir bar was added, and the mixture was stirred for 2 hours at room temperature to create a tetrahydrocurcumin-zinc-curcumin complex. It was noted that the component mixture turned from an initial yellow color at time zero into a red color by 2 hours as it became a complex. A change from yellow color to a red color is consistent with molecular changes to curcumin as zinc binds to it due to structural chromophore changes. The complex was placed into a rotoevaporator flask, and the methanol was removed to result in a red color powder matrix complex.

An aliquot of the complex was dissolved in 100% acetic acid and purified on a Sephadex G25 column with acetic acid as the running buffer. It was noted that a red color band migrated through the column while a yellow color remained bound throughout the entire column after the purification run was completed. These color banding results are consistent with the red band being a zinc complexed to curcumin and tetrahydrocurcumin while the yellow band is consistent with unreacted free curcumin and unreacted free tetrahydrocurcumin. The red color is consistent with a molecular structure change when zinc binds to diketols located in the center part curcumin and tetrahydrocurcumin molecules.

Example 7

Figure 5A:
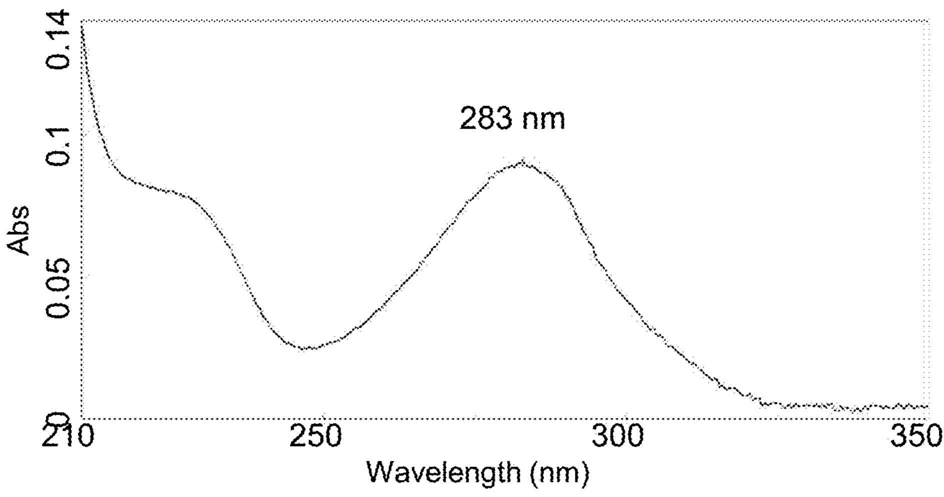
FIGS. 5A-5C. UV profiles of tetrahydrocurcumin (FIG. 5A), a tetrahydrocurcumin-Zn complex of the invention created at pH 2 (FIG. 5B), and a tetrahydrocurcumin-Zn complex of the invention created at pH 7.5 (FIG. 5C).
Figure 5B:
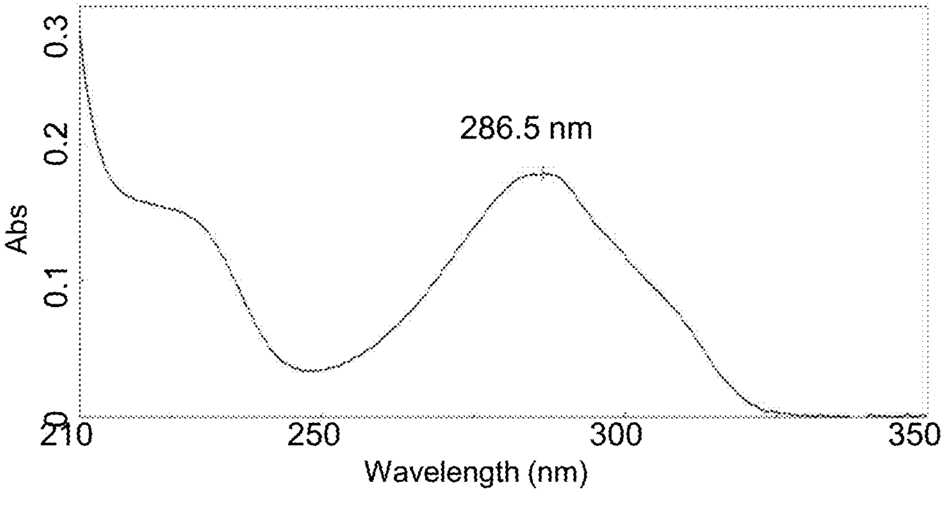
Figure 6A:
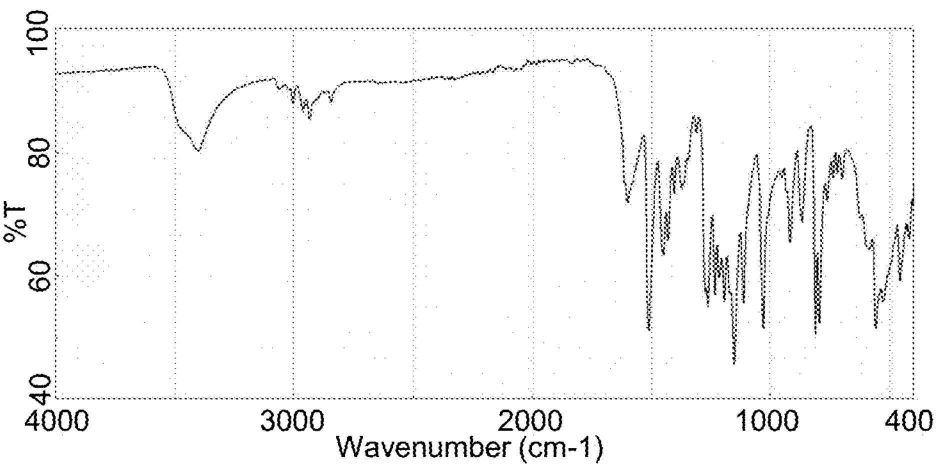
FIGS. 6A-6C. FTIR profiles of tetrahydrocurcumin (FIG. 6A), a tetrahydrocurcumin-Zn complex of the invention created at pH 2 (FIG. 6B), and a tetrahydrocurcumin-Zn complex of the invention created at pH 7.5 (FIG. 6C).
Figure 6B:
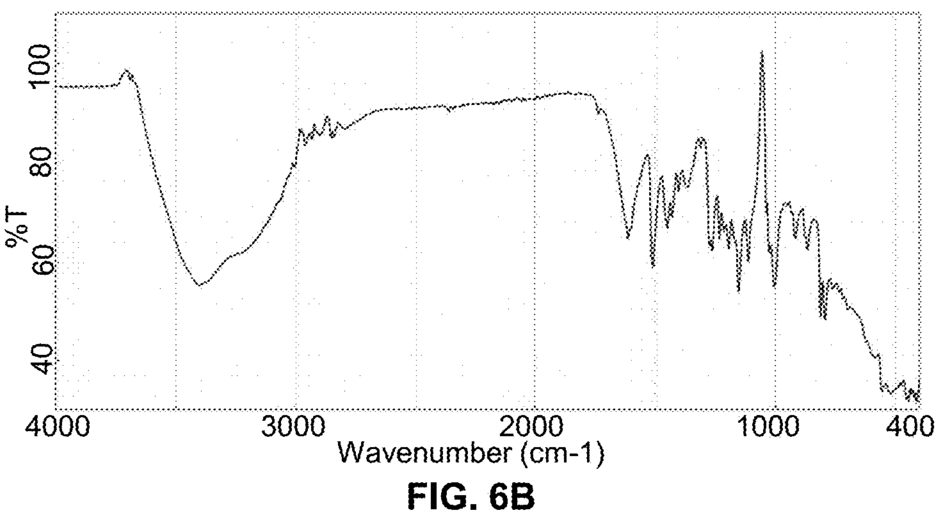

1 mole (372.4 grams) of tetrahydrocurcumin was added to 1 mole (136 grams) of $ZnCl_2$ and 1 liter of methanol was added to solvate the materials into a clear solution. This clear solution mixture was at pH 2.0. The mixture was dried into a powder by rotoevaporation, analyzed for changes in the UV profile and FTIR profile, and compared to the control tetrahydrocurcumin starting material that was not subjected to complexation with zinc. FIGS. 5A and B show a shift of the peak at 283 nm in the UV profile for the control material (FIG. 5A) to 286 nm for the pH 2.0 complex (FIG. 5B). FTIR profiles of the pH 2.0 tetrahydrocurcumin-zinc complex also revealed changes at 3397, 970, and 450 wavenumbers (FIGS. 6A and 6B). These changes are consistent with zinc binding to tetrahydrocurcumin and changing the structural conformation when complexation occurs. It is concluded that both the UV and the FTIR profile are consistent with zinc binding to tetrahydrocurcumin and causing a complexation reaction and the formation of a new molecule.

Example 8

Figure 5C:
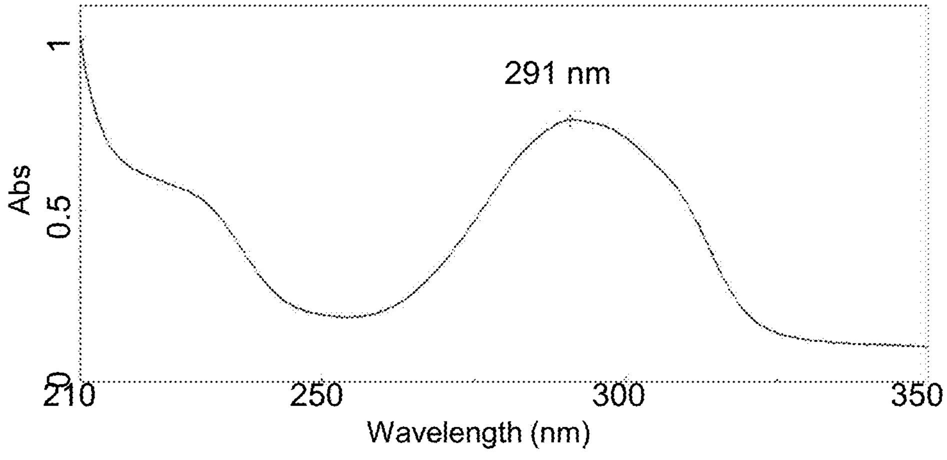
Figure 6C:
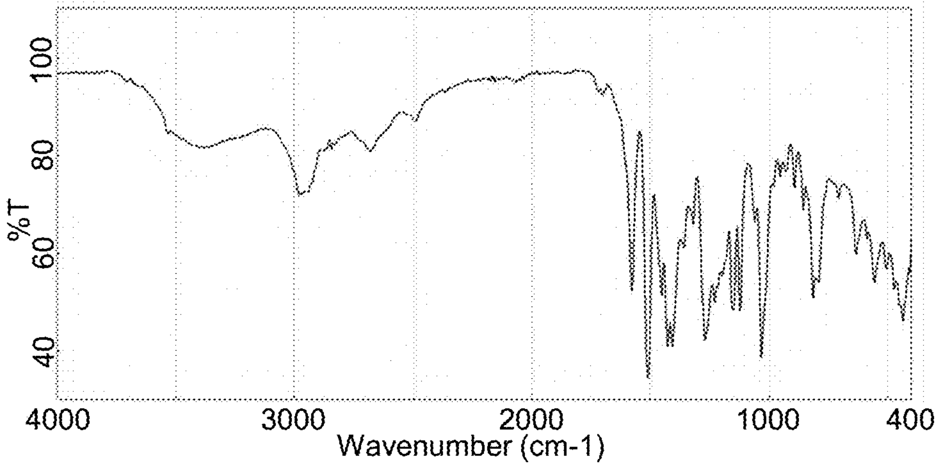
Figure 7A:
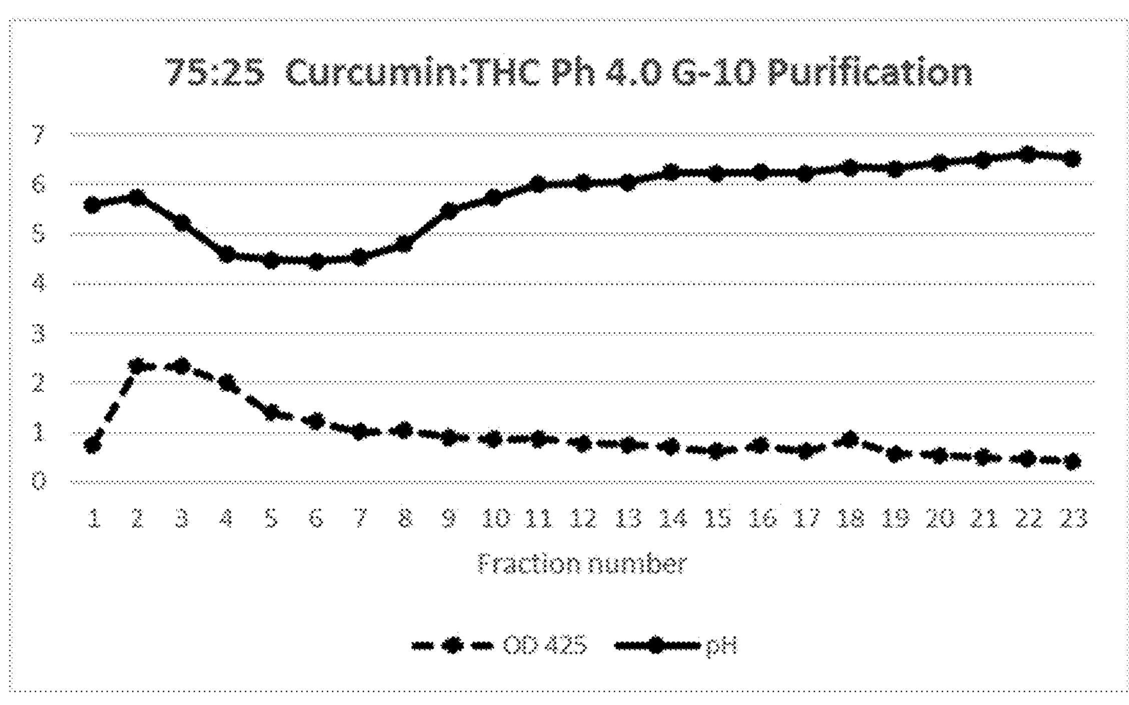
FIGS. 7A-7F. Sephadex G-10 purification of different ratios of curcumin:tetrahydrocurcumin (THC) when complexed with zinc at pH 4.0 (FIGS. 7A, 7C, and 7E) or pH 7.0 (FIGS. 7B, 7D, and 7F).
Figure 7B:
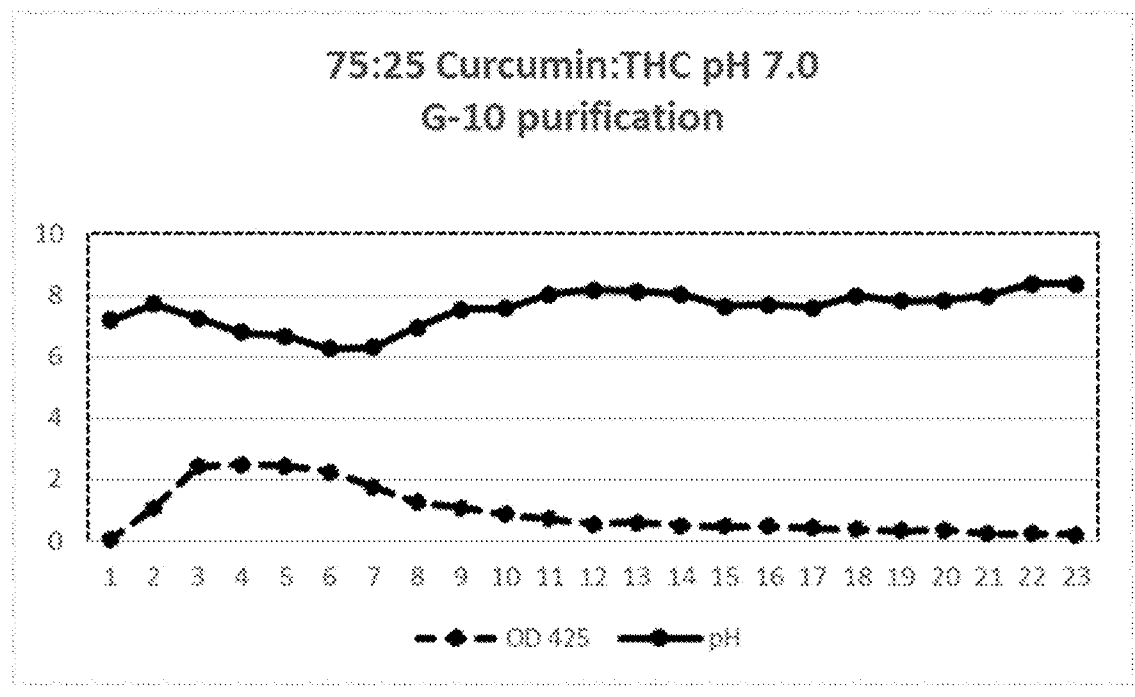
Figure 7C:
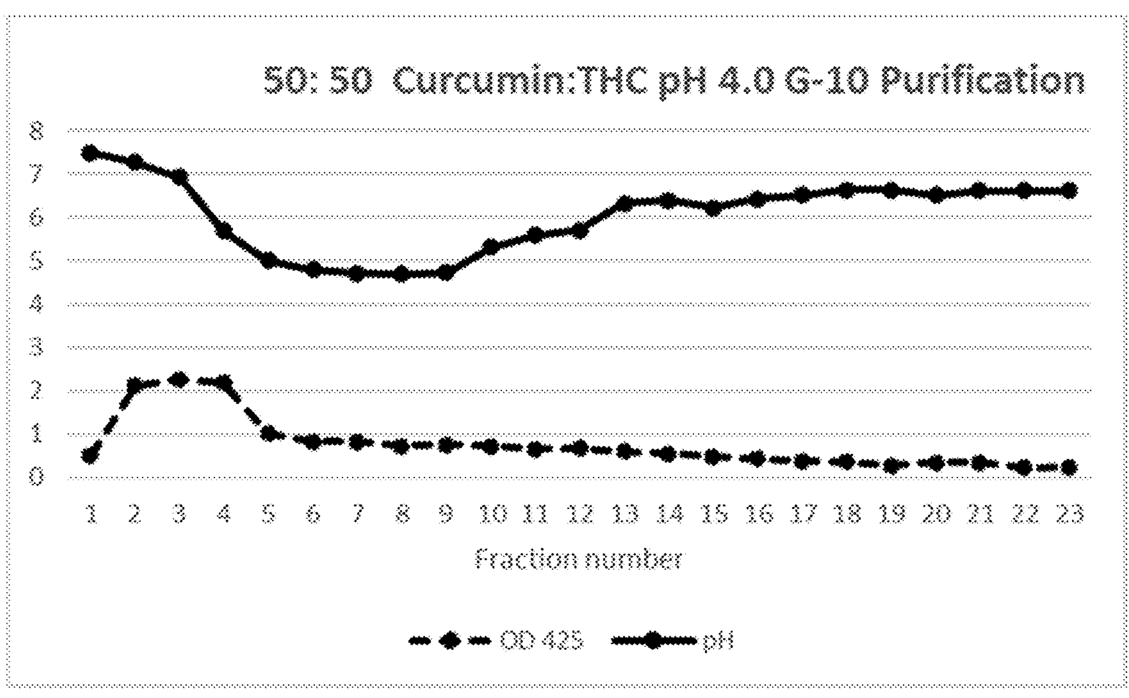
Figure 7D:
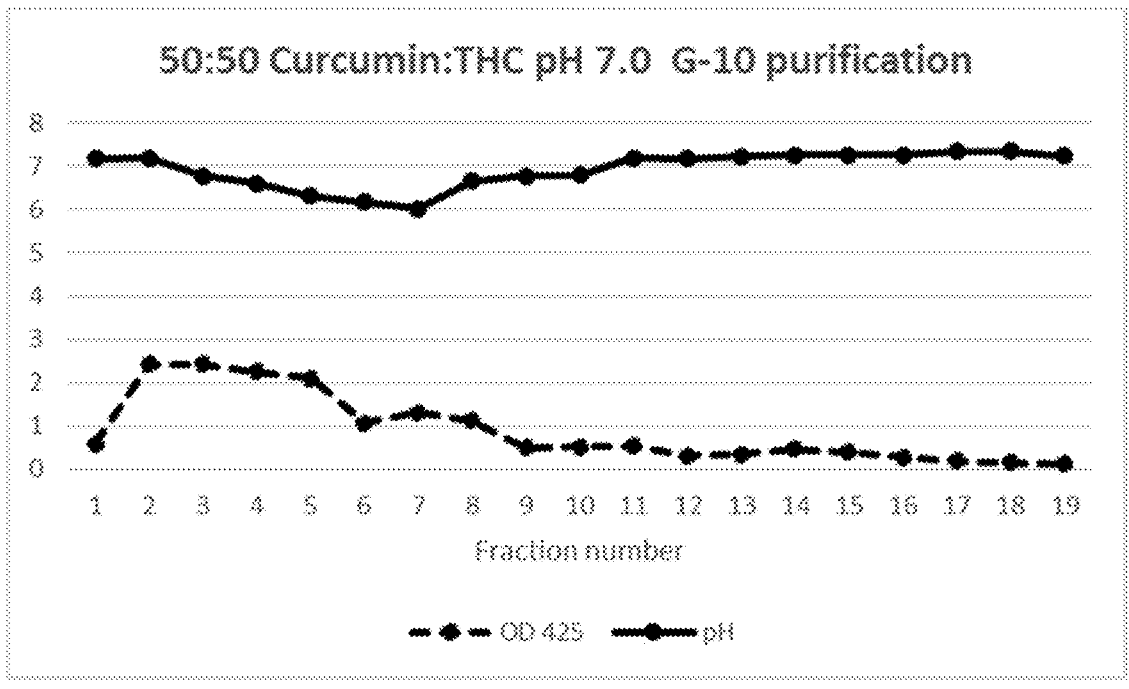
Figure 7E:
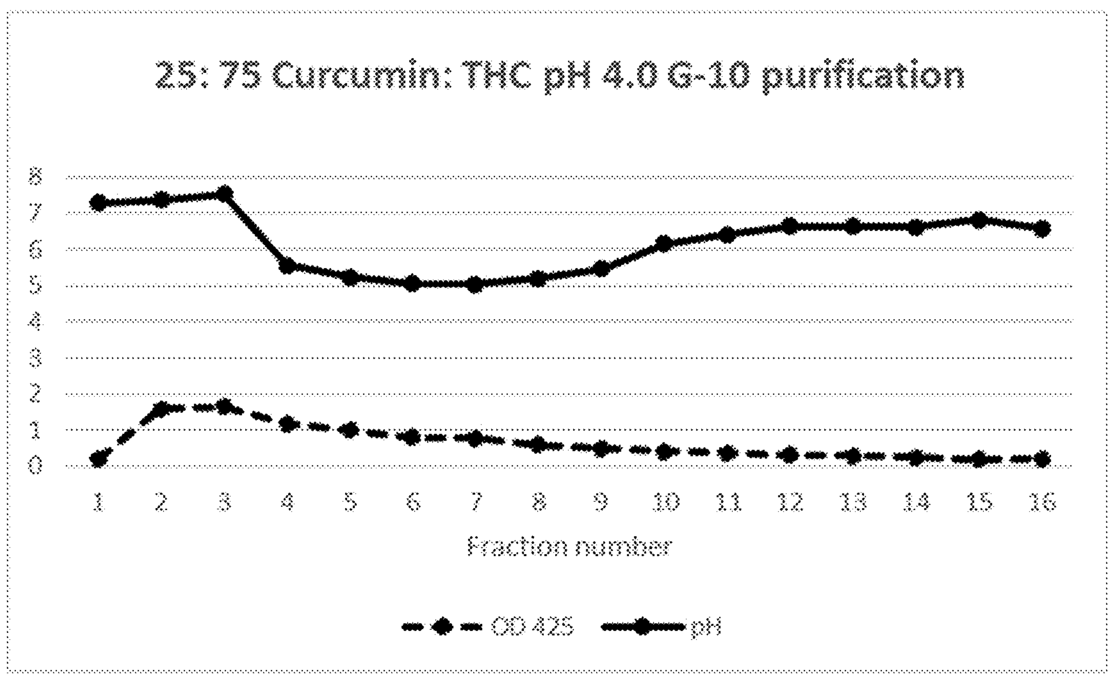
Figure 7F:
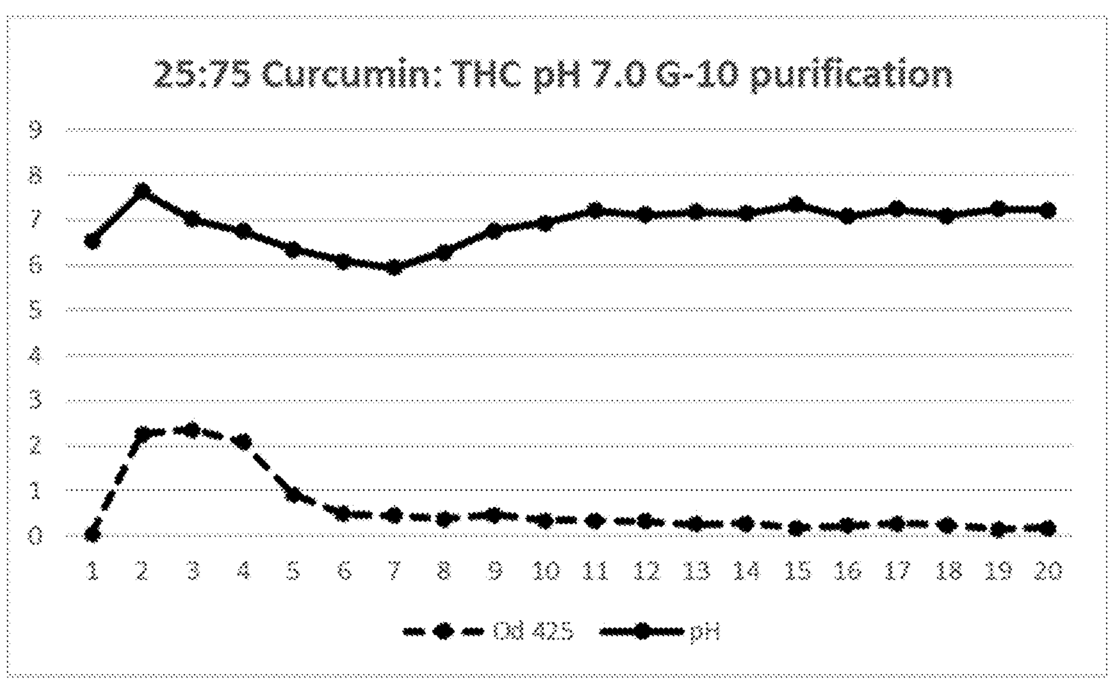

1 mole (372.4 grams) of tetrahydrocurcumin was added to 1 mole (136 grams) of $ZnCl_2$, and 1 liter of methanol was added to solvate the materials into a clear solution. This clear solution mixture was at pH 2.0. Half of this mixture was placed in a separate beaker and the pH was raised to pH 7.5 using triethylamine. It was unexpectedly noted that an immediate white precipitate occurred in the mixture when the pH was raised. Both mixtures were stirred at room temperature for 24 hours. The mixtures were dried into a powder by rotoevaporation, analyzed for changes in the UV profile and FTIR profile, and compared to the control tetrahydrocurcumin starting material that was not subjected to complexation with zinc. FIGS. 5A and 5B show a shift of the peak at 283 nm in the UV profile for the control material (FIG. 5A) to 286 nm for the pH 2.0 complex (FIG. 5B). This shift further increased to 292 nm with the pH 7.5 tetrahydrocurcumin-Zn complex material, and a broadening of the lagging side peak occurred (FIG. 5C). FTIR profiles of the pH 2.0 tetrahydrocurcumin-Zn complex revealed changes at 3397, 970, and 450 wavenumbers (FIGS. 6A and 6B). These changes are consistent with zinc binding to tetrahydrocurcumin and changing the structural conformation when complexation occurs. FTIR profiles of the pH 7.5 tetrahydrocurcumin-Zn complex revealed changes at 1576, 1426, and 2980 wavenumbers as compared to the starting tetrahydrocurcumin material (FIGS. FIGS. 6A and 6C). These changes are consistent with binding of zinc to hydroxyl groups in the central part of the structure and thus changing the structure of tetrahydrocurcumin. It is concluded that both the UV and the FTIR profiles are consistent with zinc binding to tetrahydrocurcumin and causing a complexation reaction and the formation of a new molecule. When the reaction is carried out at pH 7.5, the reaction is presumably enhanced due to changes predominately of keto into enol forms of tetrahydrocurcumin. This unexpected finding is a novel manner to improve chelation of zinc to tetrahydrocurcumin. It is concluded that zinc can complex to tetrahydrocurcumin at either pH 2.0 or pH 7.5 and change UV and FTIR profiles vs control tetrahydrocurcumin without zinc present. The data are consistent with the complexation being more efficient at pH 7.5.

Example 9

As tetrahydrocurcumin has some different biological properties than curcumin, having different ratios of tetrahydrocurcumin to curcumin in the zinc complex of the invention can extend the efficacy of the invention for different disease and health conditions. As such, the ratio of tetrahydrocurcumin to curcumin during complexation to zinc was examined. In addition, the pH during the complexation reaction was examined at acidic and at neutral pH. Ratios of 25:75, 50:50, and 75:25 of tetrahyrdocurcumin:curcumin were created by weighing out relative amounts tetrahydrocurcumin and curcumin based on molecular weights of each and mixing together to form a uniform powder. A 2-mole amount of the uniform mixed ratios of tetrahydrocurcumin: curcumin were added to a 1-mole amount of zinc chloride. One liter of methanol was added to solvate the mixture, and the pH was noted to be pH 4.0. Half of the solvated solution was removed to a different beaker, and the pH was raised to pH 7.0 using triethylamine. Raising the pH from pH 4 to pH 7 changed the color from a yellow/orange to red. All 6 sets of the mixed ratio solutions were stirred at room temperature for 24 hours. The solutions were dried to a powder by rotoevaporation and subjected to UV and FTIR analysis. The 250 mg of dried powders were dissolved in 1 ml acetone and were subsequently purified using Sephadex G-10 low pressure chromatography with a 45:55 acetone:water solvent to separate the complexed powders based on molecular weight. Absorbance at OD 425 and pH were monitored for the eluted fractions (FIGS. 7A-7F). Different color bands migrated through the column that corresponded to different molecular weights. The leading edge of the pH 7.0 complexes were dark red while lagging subsequent fractions were yellow/orange. The pH of fractions decreased with a corresponding increase of OD 425 that recovered as less OD was eluting (FIGS. 7A-7F). These data are consistent with leading edge the profile having larger molecular weight that was complexed with zinc. The lagging edge fractions are consistent with containing unbound curcumin and unbound tetrahydrocurcumin. The data indicate that various ratios of curcumin:tetrahydrocurcumin can be complexed with zinc in the invention.

Figure 8A:
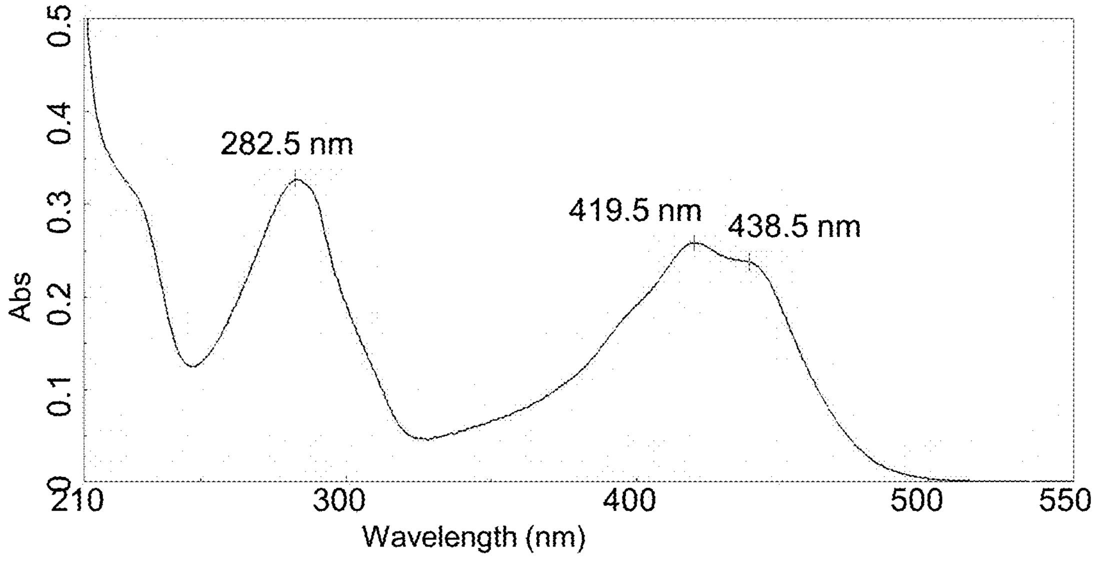
FIGS. 8A and 8B. UV profiles of Sephadex G10-purified red-colored (FIG. 8A) and yellow/white-colored (FIG. 8B) zinc complexes of curcumin and tetrahydrocurcumin generated with a 25:75 curcumin:tetrahydrocurcumin ratio.
Figure 8B:
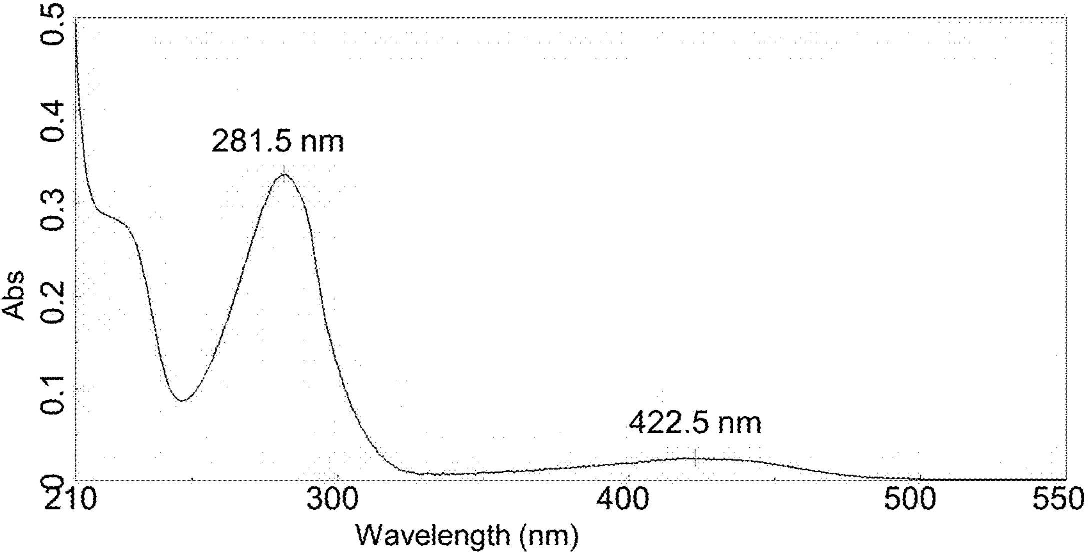
Figure 9A:
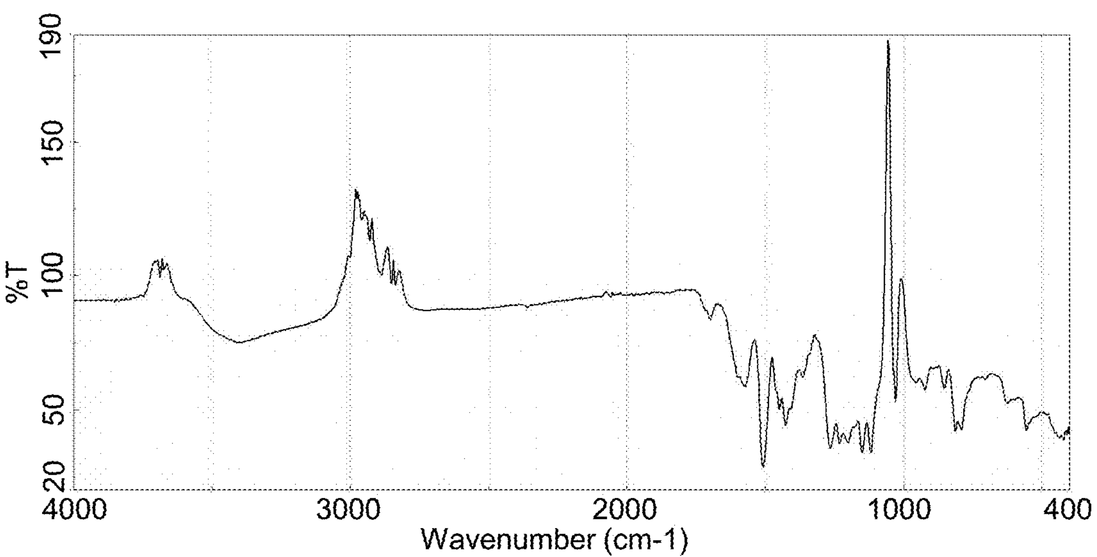
FIGS. 9A and 9B. FTIR profiles of Sephadex Gb-purified red-colored (FIG. 9A) and yellow/white-colored (FIG. 9B) zinc complexes of curcumin and tetrahydrocurcumin generated with a 25:75 curcumin:tetrahydrocurcumin ratio.
Figure 9B:
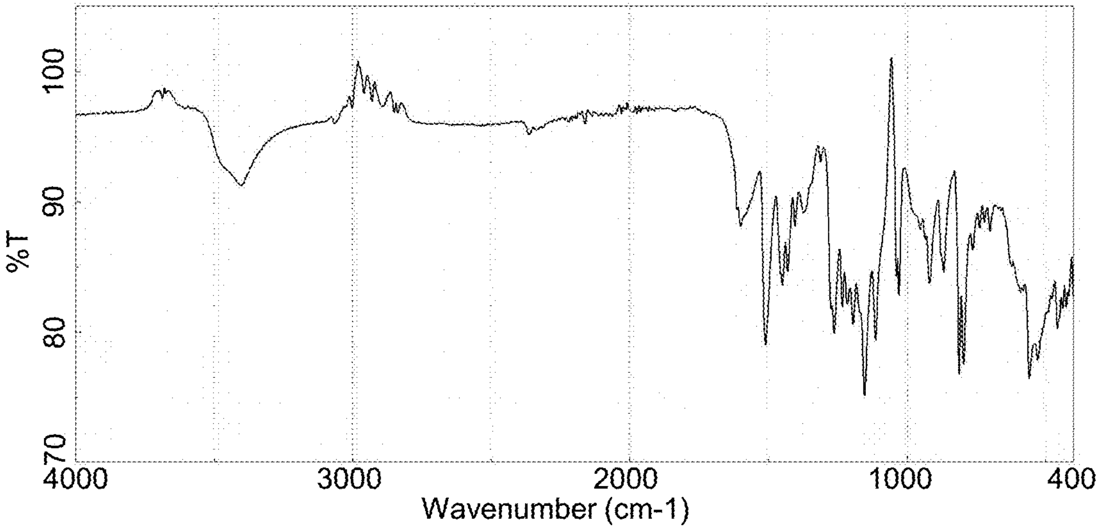

During the purification of the 25:75 curcumin:tetrahydrocurcumin ratio complex with zinc at pH 7.0, the leading edge fractions when dried contained both red crystals and yellow/white crystals. These crystals are consistent with the formation of novel tetrahydrocurcumin-zinc-curcumin complexes of the invention. These crystals were subjected to UV (FIGS. 8A and 8B) and FTIR analysis (FIGS. 9A and 9B).

The UV and FTIR of purified fractions are consistent with the formation of a novel molecular complex of tetrahydrocurcumin and curcumin concurrently bound to zinc. Different ratios of curcumin to tetrahydrocurcumin can be utilized when binding to zinc. Raising the pH of the reaction from acidic conditions to neutral conditions allows for the change of the predominant keto forms of the reactants to an enol form. This change unexpectedly allows for more efficient binding of the divalent zinc concurrently to both curcumin and tetrahydrocurcumin with subsequent greater changes observed in UV and FTIR profiles.

Example 10

Figure 10A:
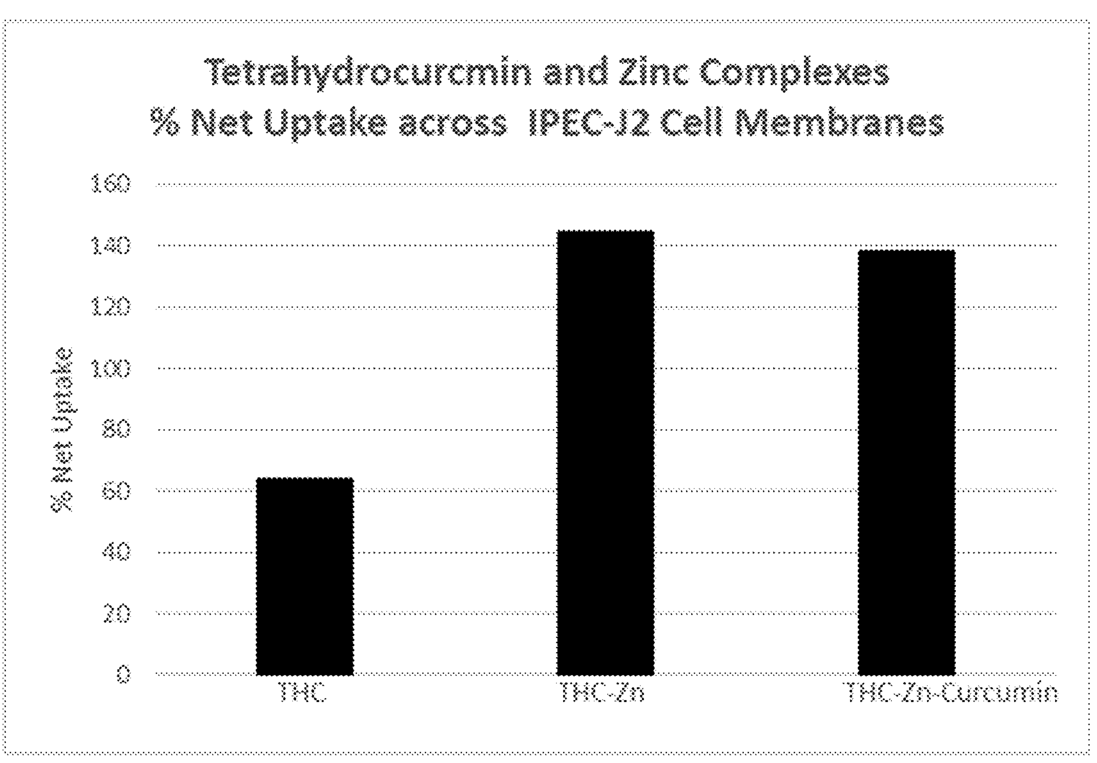
FIGS. 10A and 10B. % net uptake of tetrahydrocurcumin (THC) and zinc complexes thereof (FIG. 10A) and curcumin and zinc complexes thereof (FIG. 10B) across IPEC-J2 cell membranes as determined by HPLC.
Figure 10B:
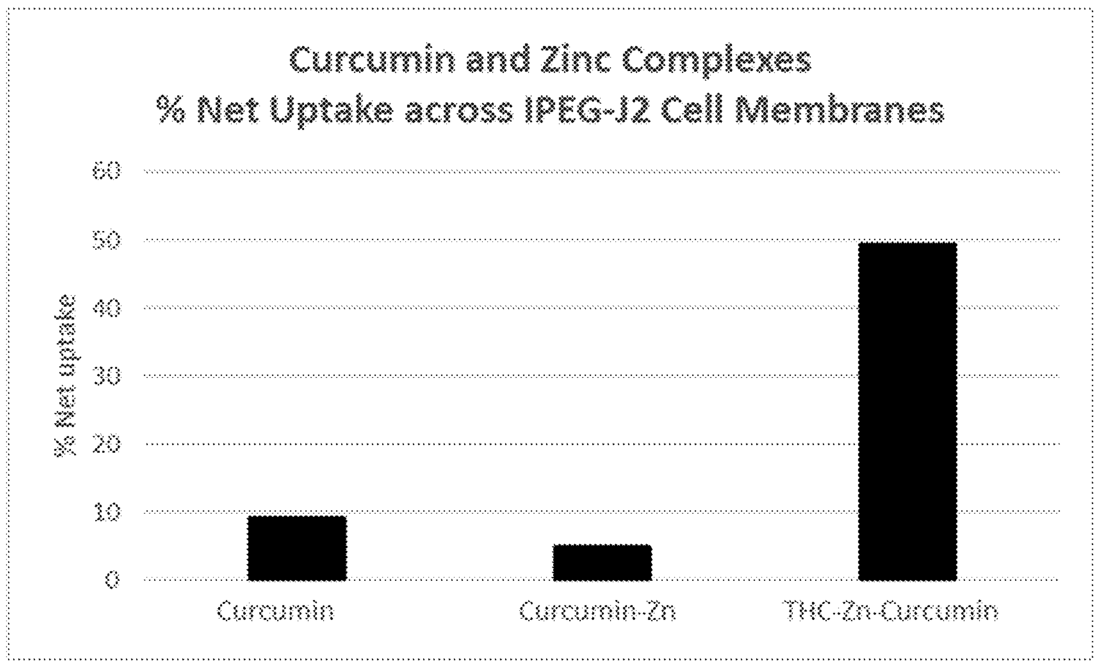

Cellular transport studies of the invention were performed in 6-well transwell plates using triplicate wells for each timepoint to show that the complexes of the invention cross cell membranes to become bioavailable. Pig intestinal IPEC J2 cells were used and grown to confluence using DME medium and 5% fetal calf serum. The cells were washed with saline. One milliliter of saline was present in the bottom wells at all times. Curcumin, tetrahydrocurcumin, and a 75:25 mixture of curcumin:tetrahydrocurcumin were complexed with $ZnCl_2$ as described in Examples 7 and 9. 2.0 mg of curcumin, curcumin-Zn complex, tetrahydrocurcumin, tetrahydrocurcumin-Zn complex, and tetrahydrocurcumin-Zn-curcumin complex were solubilized in saline with 5.0% DMSO, and 1 ml was placed in the top wells and incubated for 2 hours at 37° C. OD 425 nm and OD 220 nm were measured in the top and bottom wells spectrophotometrically or by HPLC. OD 425 nm is representative of curcumin, curcumin-Zn complexes, and tetrahydrocurcumin-Zn-curcumin complexes. OD 220 nm is representative of tetrahydrocurcumin and tetrahydrocurcumin-Zn complexes. The % net uptake of the respective agents were calculated by summing the OD in the upper and lower wells and then dividing the sum by the bottom well OD and graphed as shown in FIG. 10A. The data indicate that zinc improved the uptake of tetrahydrocurcumin by >2 fold. A similar amount of uptake was observed in the tetrahydrocurcumin-Zn-curcumin complex as compared to the tetrahydrocurcumin-Zn complex. The data indicate in this particular cell culture system that some curcumin crossed membranes, with or without the presence of zinc. However, when the curcumin was complexed to zinc in the presence of tetrahydrocurcumin, an unexpected 5-fold increase occurred as seen in FIG. 10B. This is consistent with the efficacy of the complexes of the invention to improve bioavailability of curcumin presumably by the presence of tetrahydrocurcumin being complexed to the curcumin to allow better uptake.

Example 11

Figure 11:
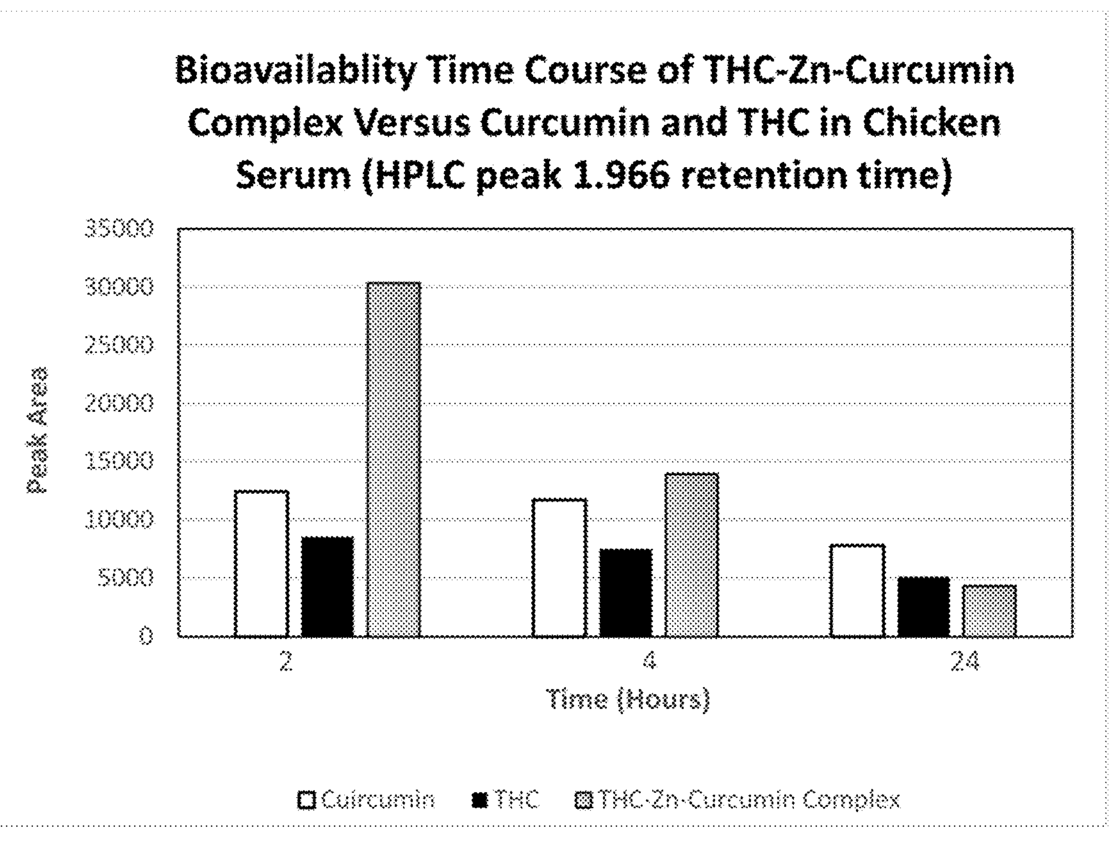
FIG. 11. Time course of bioavailability in blood of curcumin, tetrahydrocurcumin (THC), and a THC-zinc-curcumin complex.
Figure 12A:
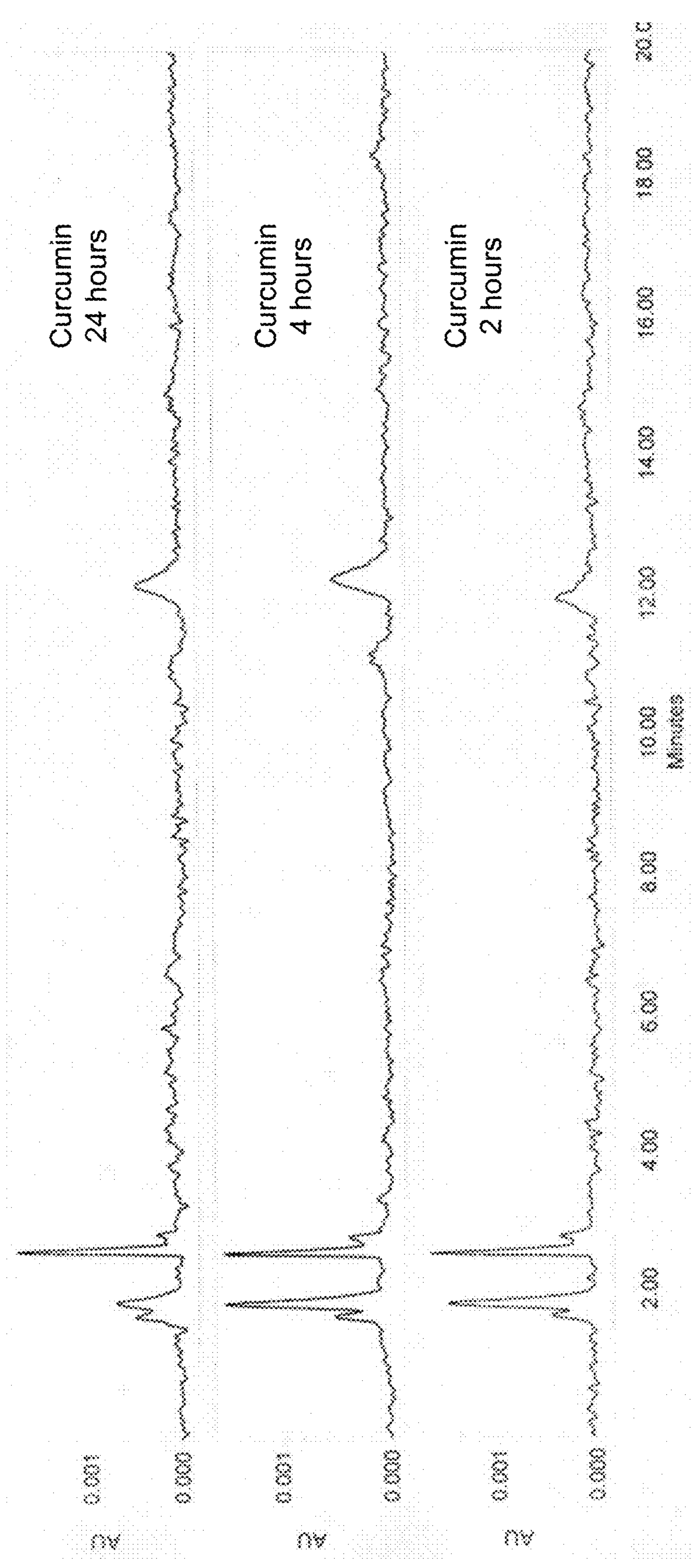
FIGS. 12A-12C. HPLC at 280 nm of serum of chickens fed curcumin (FIG. 12A), tetrahydrocurcumin-zinc-curcumin complex (THC-Zn-Curcumin) (FIG. 12B), and tetrahydrocurcumin (THC) (FIG. 12C) at 2-hour, 4-hour, and 24-hour timepoints after feeding.
Figure 12B:
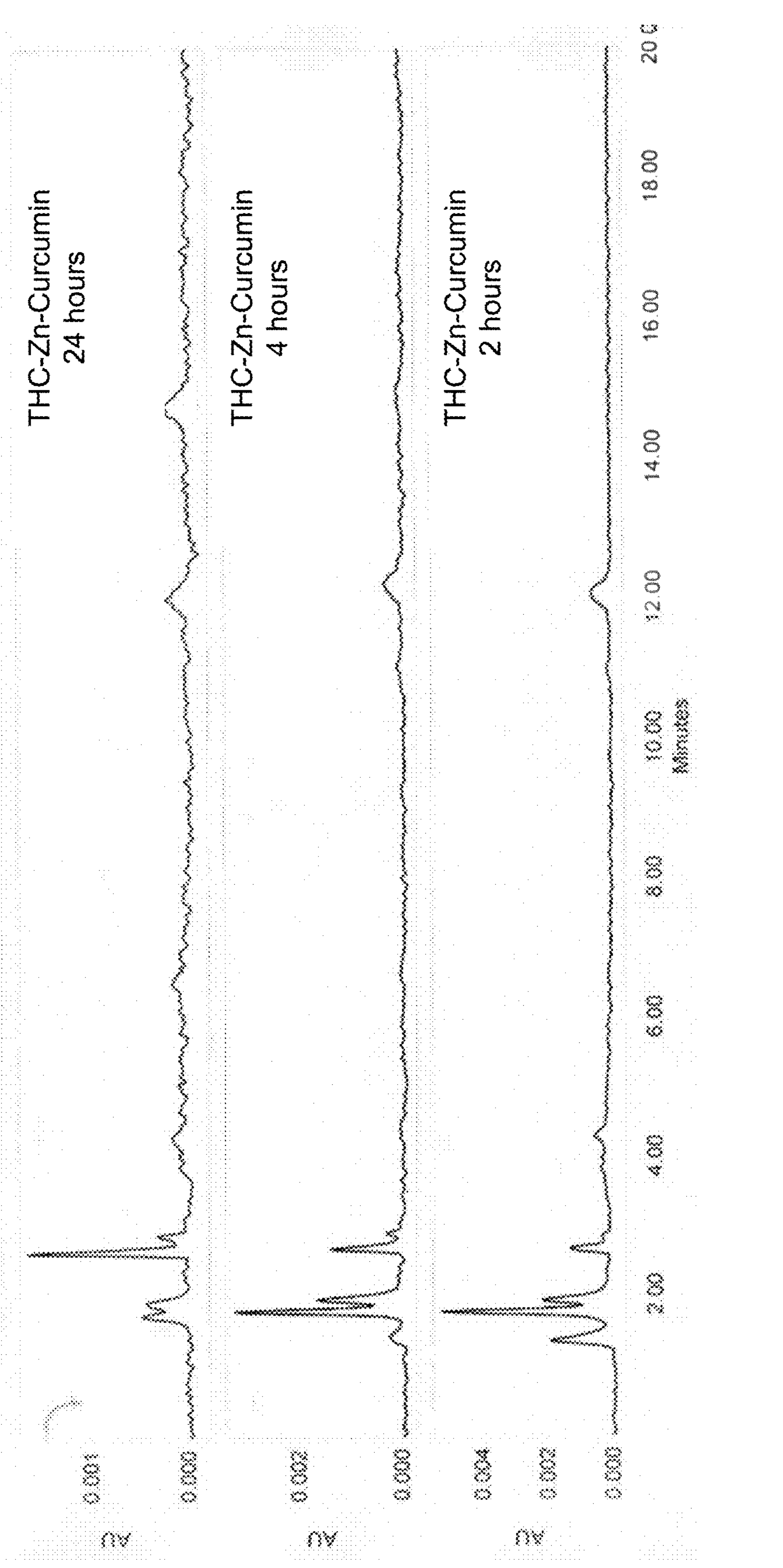
Figure 12C:
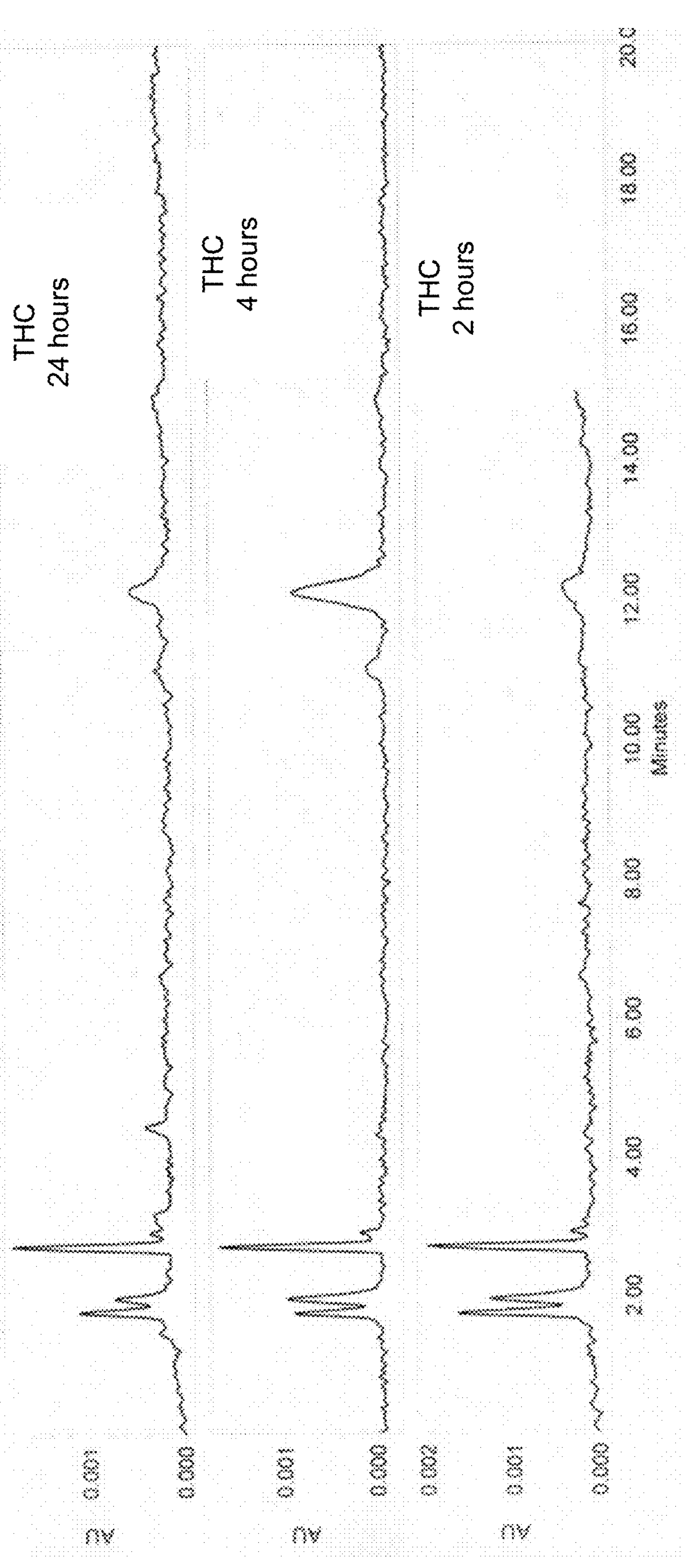
Figure 13A:
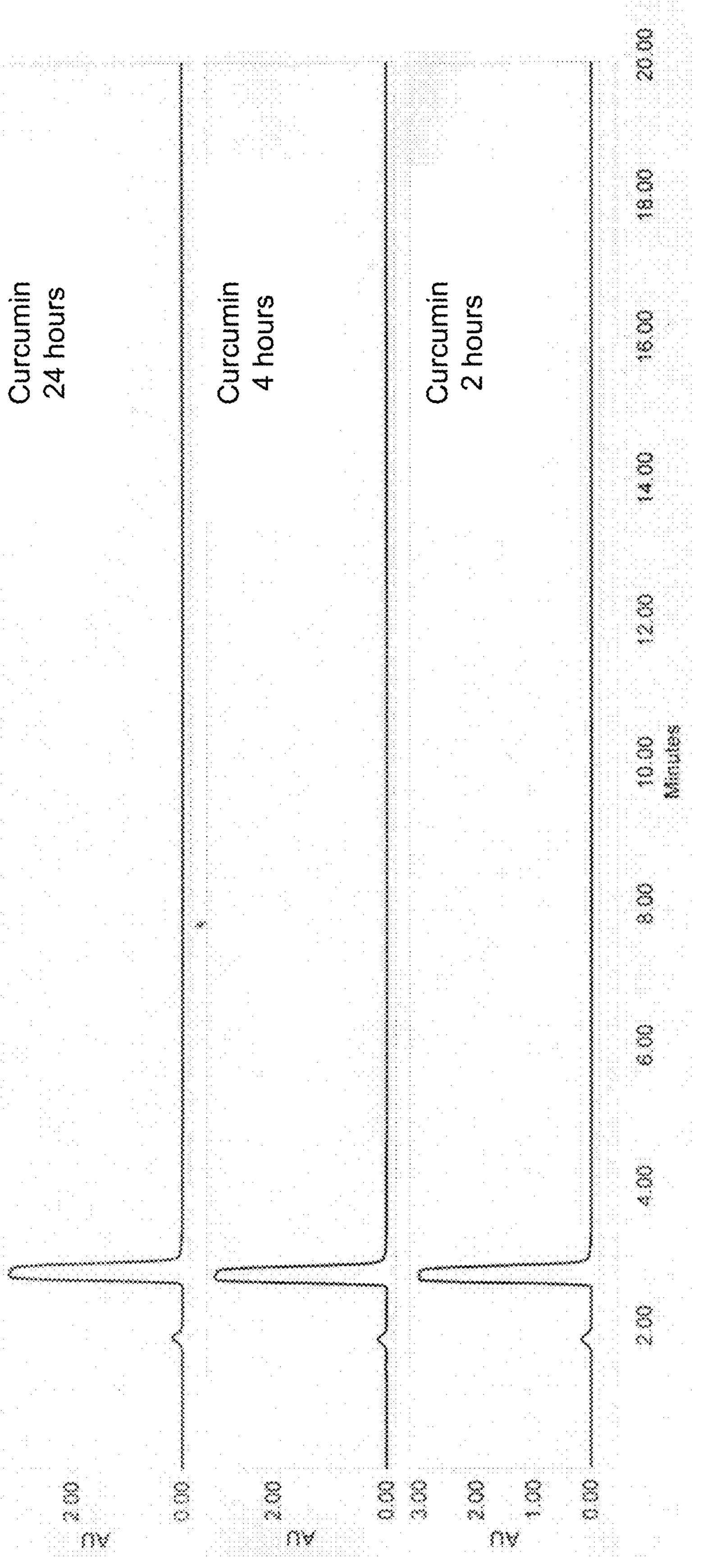
FIGS. 13A-13C. HPLC at 425 nm of serum of chickens fed curcumin (FIG. 13A), tetrahydrocurcumin-zinc-curcumin complex (THC-Zn-Curcumin) (FIG. 13B), and tetrahydrocurcumin (THC) (FIG. 13C) at 2-hour, 4-hour, and 24-hour timepoints after feeding.
Figure 13B:
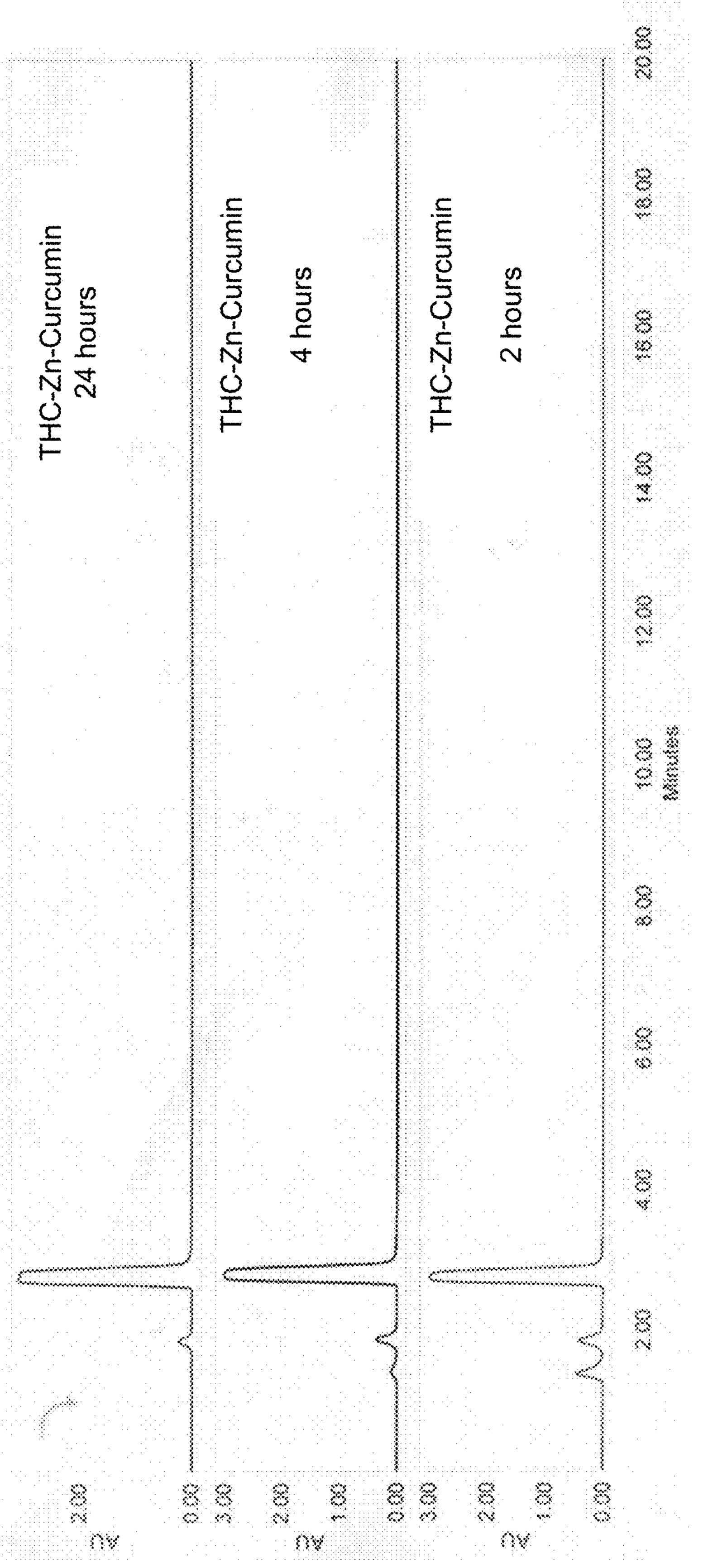
Figure 13C:
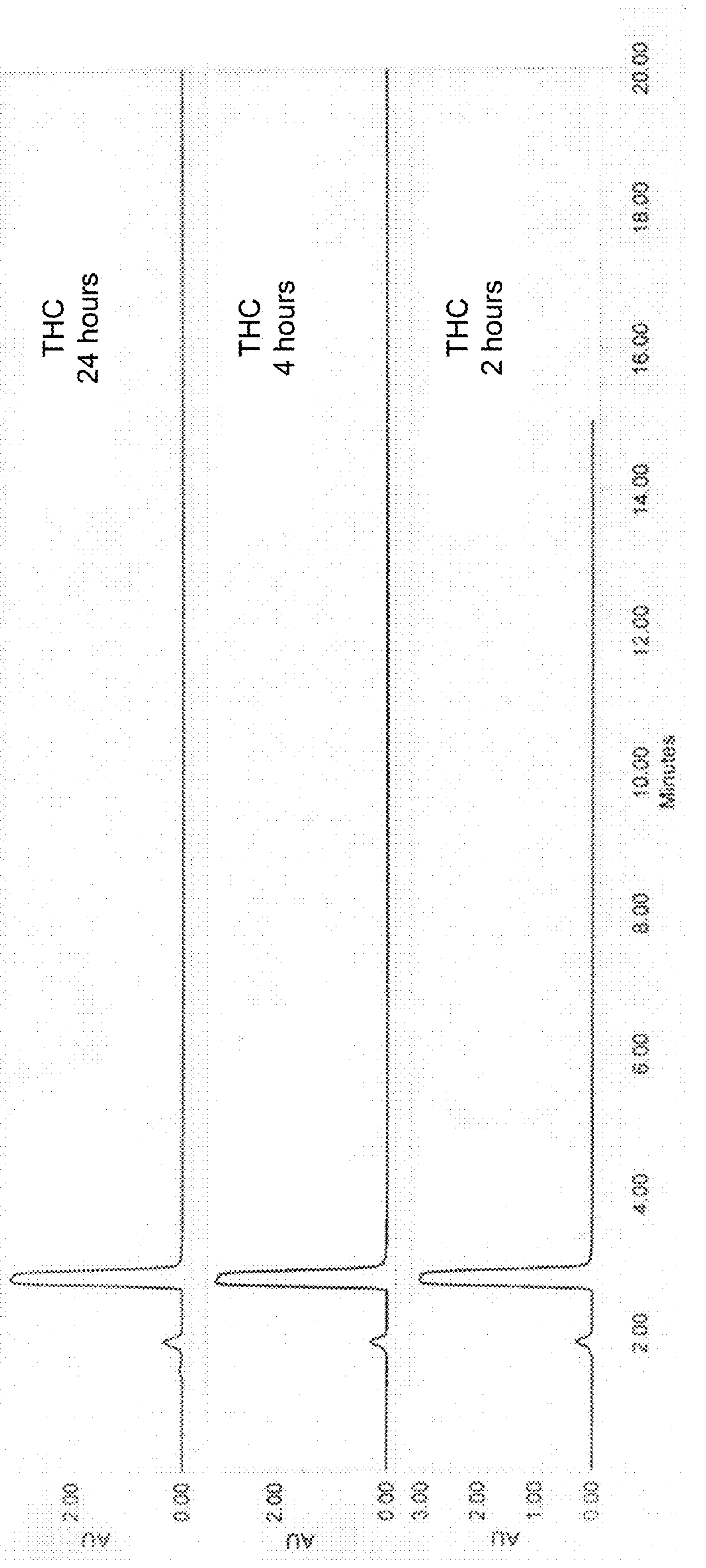

An animal trial was conducted to determine the bioavailability of the complexes of the invention in blood. One gram of curcumin was suspended in 5 ml of water and placed into a syringe. One gram of tetrahydrocurcumin was suspended in 5 ml of water and placed into another syringe. One gram of a tetrahydrocurcumin-Zn-curcumin complex of the invention as created in Example 9 was suspended in 5 ml of water and placed into another syringe. Three chickens (Rhode Island Red) that were each 2 years old weighing 5 pounds were selected, and 1 ml of blood was removed from the wing vein for baseline measurements. The blood was allowed to clot and the plasma was removed by centrifugation for subsequent baseline analysis. The chickens were allowed to rest overnight. The contents of each of the respective syringes were then administered to separate chickens via the mouth, ensuring that the contents were consumed. Blood was removed at 2, 4, and 24 hours from each bird and allowed to clot. The recovered serum was mixed with equal volumes of acetone via vortexing for 30 seconds and then centrifuged to remove proteins in the pellet while recovering curcumin, tetrahydrocurcumin, or the elements of the tetrahydrocurcumin-Zn-curcumin complex in the supernatant. The supernatants from each time point were analyzed by standard HPLC methods for the presence of curcumin, tetrahydrocurcumin, or the tetrahydrocurcumin-Zn-curcumin complex at 280 nm and 425 nm wavelengths. The results show that peaks due to curcumin, tetrahydrocurcumin, or the tetrahydrocurcumin-Zn-curcumin complex could be seen at the 2-hour, 4-hour, and 24-hour timepoints in each of the respective samples. However, the tetrahydrocurcumin-Zn-curcumin complex had 2 to 3 times as much peak area at the 1.996 min chromatogram retention peak as curcumin or tetrahydrocurcumin for the 2-hour timepoint (FIG. 11). This result is consistent with an increased bioavailability of the tetrahydrocurcumin-Zn-curcumin of the invention in an animal by 2 hours as compared to just curcumin or tetrahydrocurcumin. Furthermore, the data show that the tetrahydrocurcumin-Zn-curcumin complex is metabolized over time as evidenced by the disappearance of HPLC peaks and the appearance of new HPLC peaks in the serum at 24 hours, as seen in chromatograms analyzed at 280 nm (FIGS. 12A-12C) and 425 nm (FIGS. 13A-13C). This unexpected result is consistent with an increased bioavailability and increased longevity of the tetrahydrocurcumin-Zn-curcumin complex of the invention in blood not seen with curcumin alone or tetrahydrocurcumin alone. The data also show acute safety of the invention at 1 g/lb. body weight, as the 5-lb birds did not die nor show any ill effects when orally ingesting 1 gram of the invention.

Example 12

Figure 14A:
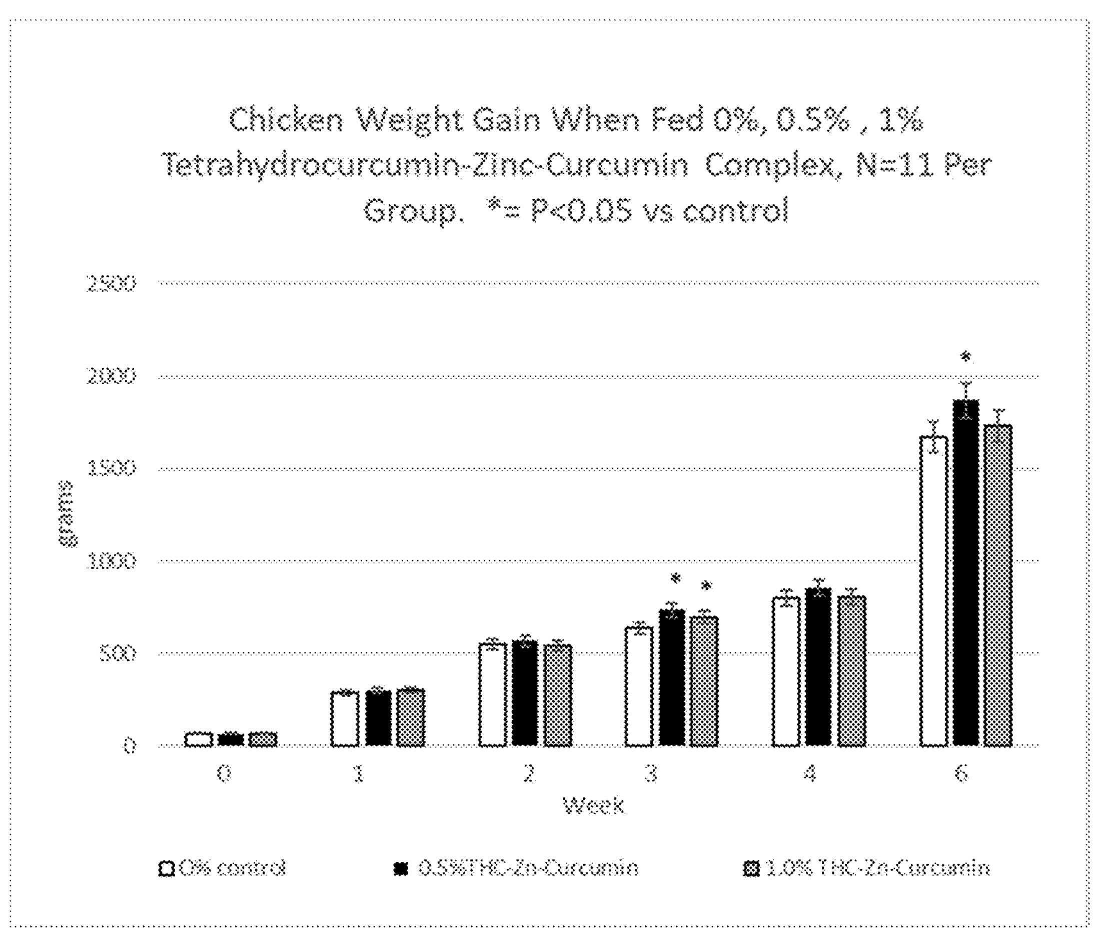
FIGS. 14A and 14B. Average weights (FIG. 14A) and average feed conversion rates (FIG. 14B) of chickens fed 0% w/w, 0.5% w/w, or 1% w/w of tetrahydrocurcumin-zinc-curcumin complex for six weeks.

A live animal trial was conducted to determine the effects of a tetrahydrocurcumin-Zn-curcumin complex to improve health. Increased weight gain in newborn chickens receiving the tetrahydrocurcumin-Zn-curcumin complex as compared to control newborn chickens that did not receive the tetrahydrocurcumin-Zn-curcumin complex in the same time frame is a measure of improved health and efficacy of the invention. The trial was conducted over a 6-week period. Three groups of N=11/group day-old chickens (Cornish cross males) were placed in three identical pens with identical size (5 foot×5 foot), lighting, heat, water, and feeder apparatus. One chicken group served as control, one group received 0.5% w/w of the tetrahydrocurcumin-Zn-curcumin complex mixed into the feed, and another group received 1.0% w/w of the tetrahydrocurcumin-Zn-curcumin complex mixed into the feed. The tetrahydrocurcumin-Zn-curcumin complex used in the trial was the powder created by mixing 75% curcumin with 25% tetrahydrocurcumin and complexed with zinc chloride in a 2:1 molar ratio as described in Example 9. The feed used throughout the trial was standard poultry feed mash to ensure uniform mixing of the invention. Chickens were weighed on weekly basis and the amount of feed consumed was recorded. Results are shown in FIG. 14A. The results indicated that chickens that received 0.5% of the tetrahydrocurcumin-Zn-curcumin complex in their feed statistically weighed more than the control birds by week 3 and at the end of trial ($p<0.05$). Birds that received 1% of the tetrahydrocurcumin-Zn-curcumin complex also weight more than control birds at week 3 ($p<0.05$) although unexpectantly not as much as birds that received 0.5%.

Figure 14B:
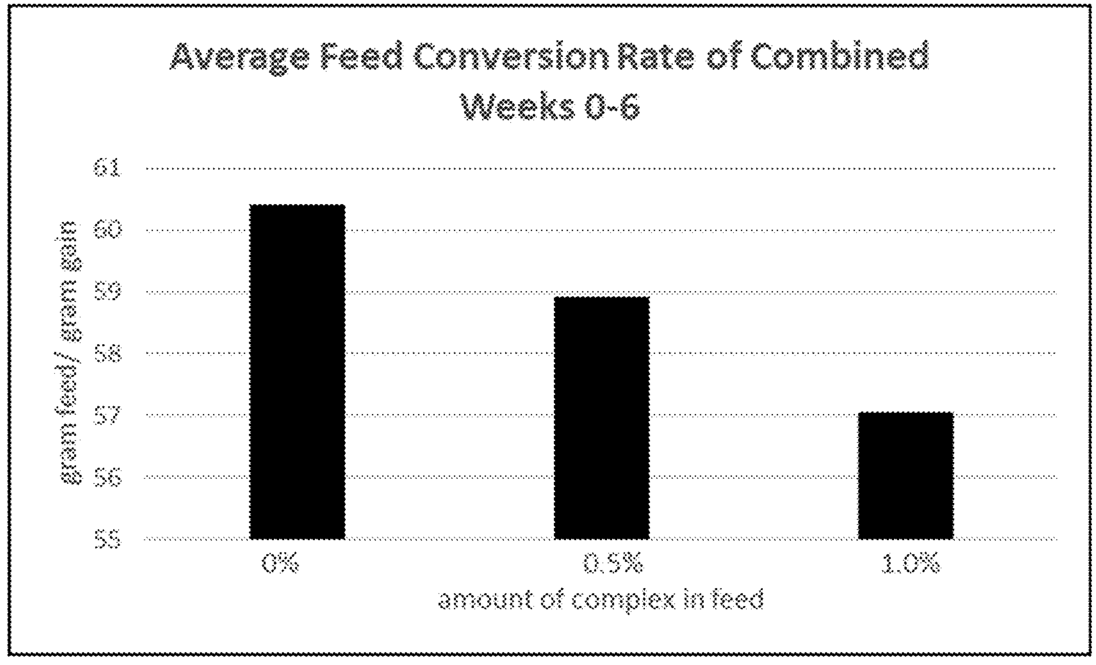

The feed conversion ratio (FCR) was calculated on a weekly basis for the different groups for the amount of feed consumed relative to the amount of weight gain. The averages of the weekly FCRs for the entire trial from week 0 to week 6 are reported in graph FIG. 14B. The data indicate that birds receiving 0.5% of the tetrahydrocurcumin-Zn-curcumin complex in feed had a lower and thus better FCR than the control group over the course of the trial. The group receiving 1.0% of the tetrahydrocurcumin-Zn-curcumin complex had a lower and even better FCR than the 0.5% group.

The results of the feed trial with the use of the tetrahydrocurcumin-Zn-curcumin complex indicate the efficacy of the invention for improving weight gain in chicken in a statistically significant manner. As weight-gain in chickens is related to overall health, these data are consistent with the complexes of the invention to improve overall health in animals. The data are consistent with the complexes of the invention reducing oxidative stress and modifying the gut microbiome in a favorable manner that allows for improved FCR in chickens or other animals. The data also show favorable chronic use safety of the invention, as no birds died or showed any ill effects as result of ingesting the composition on a daily basis for 6 weeks fed at approximately 5 g/lb. body weight. This is about 100× the fed level seen in humans for curcumin of 0.05 g/lb. body weight for safe chronic ingestion, thus indicating safety of chronic consumption of the invention.

Example 13

Levels of certain cytokines in serum have been used as a measure of general health in animals. A live animal trial was conducted to determine the effects of a tetrahydrocurcumin-zinc-curcumin complex on cytokine levels in serum. The cytokines of interleukin 1-beta (IL-1-beta), interleukin 6 (IL-6), interleukin 10 (IL-10), and interferon gamma were measured at the end of a 6-week period in newborn chickens receiving the tetrahydrocurcumin-zinc-curcumin complex on a daily basis as compared to control newborn chickens that did not receive the tetrahydrocurcumin-zinc-curcumin complex in the same time frame. The trial was conducted over a 6-week period and was part of the weight gain trial described above in Example 12. Three groups of N=3/group day-old chickens (Cornish cross males) were placed in three identical pens with identical size (5 foot×5 foot), lighting, heat, water, and feeder apparatus. One chicken group served as a control, one group received 0.5% w/w of the tetrahydrocurcumin-zinc-curcumin complex mixed into the feed, and another group received 1.0% of the tetrahydrocurcumin-zinc-curcumin complex mixed into the feed. The tetrahydrocurcumin-zinc-curcumin complex used in the trial was a powder created by mixing 75% curcumin with 25% tetrahydrocurcumin and complexed with zinc chloride in a 2:1 molar ratio as described in Example 9. The feed used throughout the trial was standard poultry feed mash to ensure uniform mixing of the invention.

Figure 15A:
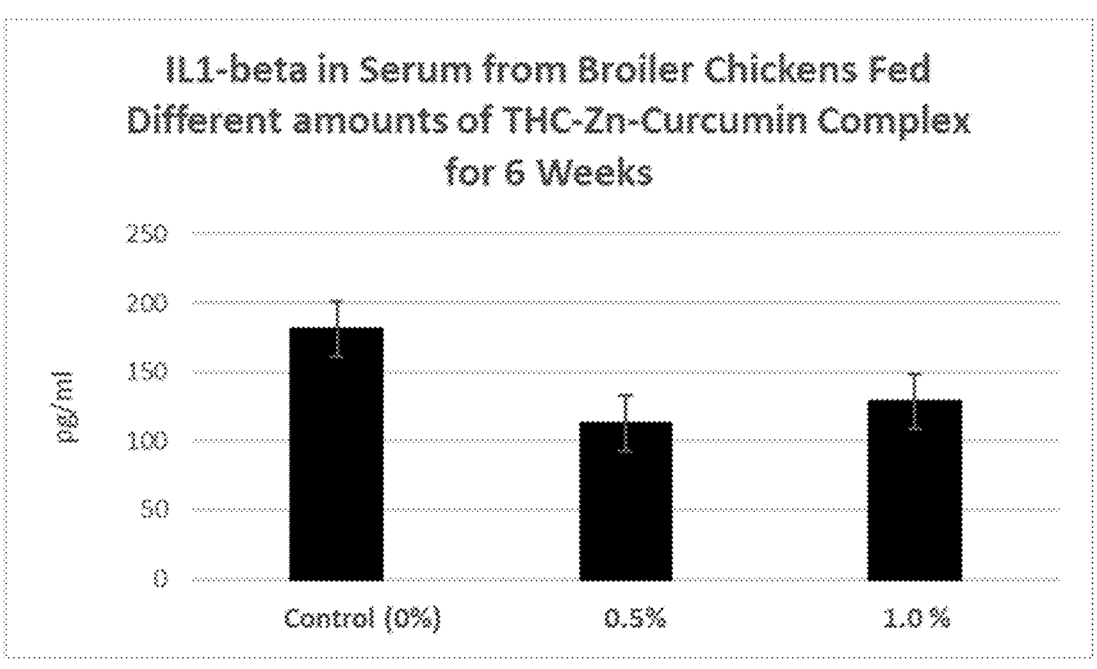
FIGS. 15A-15D. Levels of IL-1-beta (FIG. 15A), IL-6 (FIG. 15B), IL-10 (FIG. 15C), and interferon gamma (FIG. 15D) in chickens fed 0% w/w, 0.5% w/w, or 1% w/w of tetrahydrocurcumin-zinc-curcumin complex for six weeks.
Figure 15B:
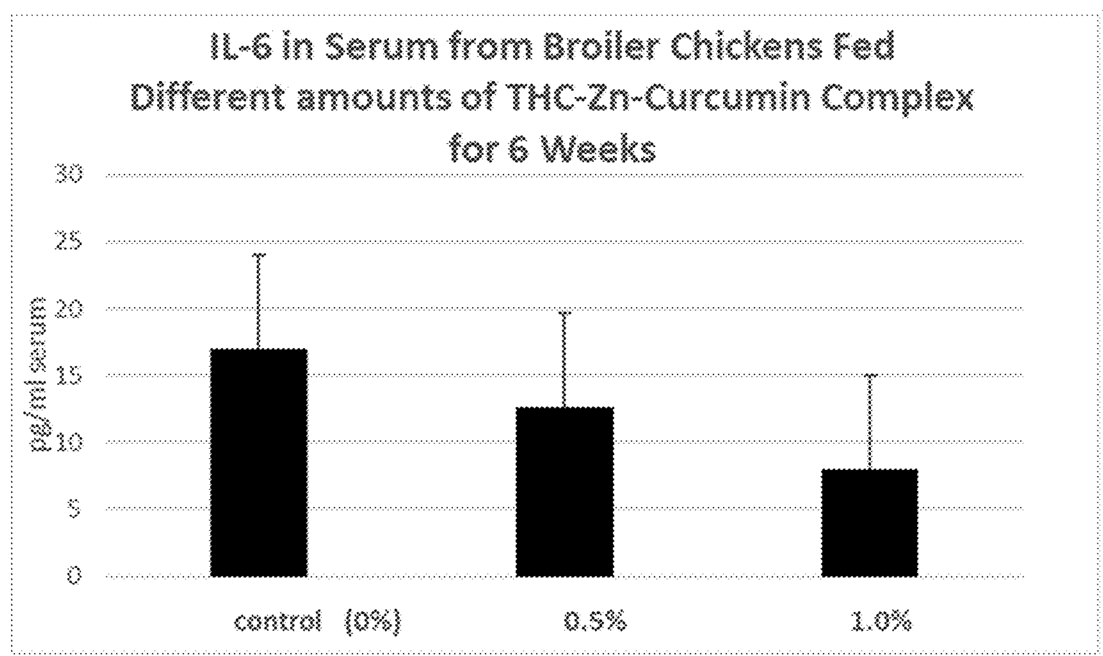
Figure 15C:
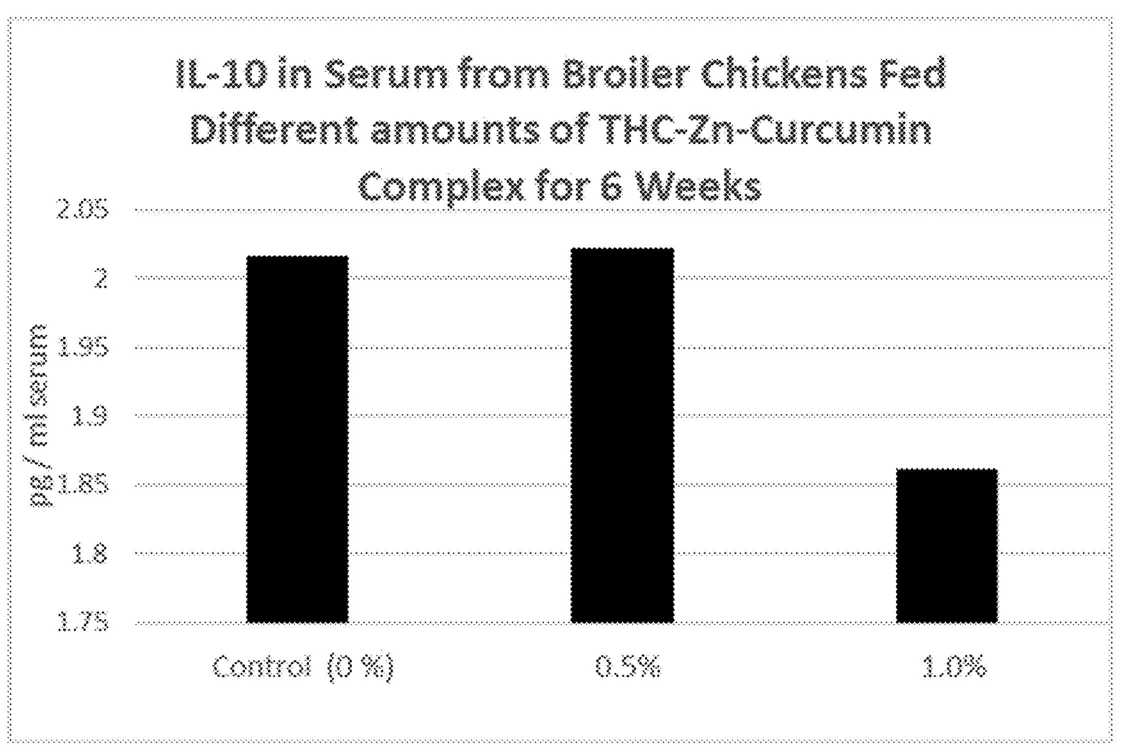
Figure 15D:
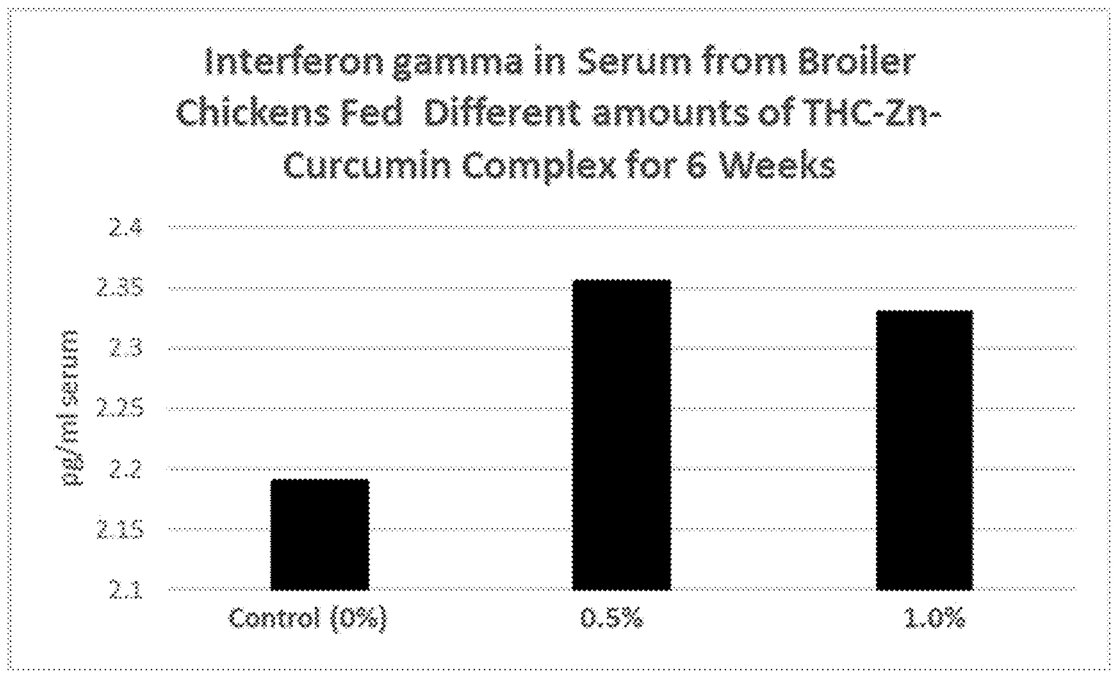

At the end of the 6 week period, blood samples were taken and allowed to clot into serum. The serum was tested by commercial ELISA kits (Cusbio) specific for chicken IL1-beta, chicken IL-6, chicken IL-10, and chicken interferon gamma using the directions from the manufacture. As shown in FIGS. 15A-15D, administration of the tetrahydrocurcumin-zinc-curcumin complex reduced the amount of IL-1-beta (FIG. 15A) and IL-6 (FIG. 15B) circulating in the blood of the chickens but did not affect the amounts of IL-10 (FIG. 15C) or interferon gamma (FIG. 15D).

These results are consistent with administration of the tetrahydrocurcumin-zinc-curcumin complex being able to block the production of the pro-inflammatory cytokines IL-1 beta and IL-6. This reduction is also consistent with the increased growth and weight gain observed in these chickens compared to control birds as described in Example 12. Having lower amounts pro-inflammatory cytokines present allows for healthier growth and increased weight gain since the animal can expend its energy in productive ways for weight gain.

The lack of a change with interferon gamma and IL-10 levels is consistent with the birds in the trial lacking active viral infections at the beginning and throughout the trial. Interferon gamma and IL-10 levels tend to be elevated if viral diseases are present. Because no obvious viral diseases were present in these birds at the beginning and throughout the trial, it is not surprising that administration of tetrahydrocurcumin-zinc-curcumin complex did not alter the levels of these cytokines.

Example 14

The antioxidant activity of a tetrahydrocurcumin-Zn-curcumin complex of the invention was measured and compared to curcumin and tetrahydrocurcumin. A standard DPPH (2,2-diphenyl-1-picryl-hydrazyl-hydrate) antioxidant assay was used to predict antioxidant activities, for example, by mechanisms in which antioxidants act to inhibit lipid oxidation. The assay scavenges the DPPH radical and therefore determines free radical scavenging capacity of test subjects. The test subjects were administered the tetrahydrocurcumin-Zn-curcumin, curcumin, or tetrahydrocurcumin. The tetrahydrocurcumin-Zn-curcumin was made as in Example 9 with a 25:75 ratio of tetrahydrocurcumin: curcumin at pH 4.0. The curcumin controls and tetrahydrocurcumin controls were from the same starting material used to make the tetrahydrocurcumin-Zn-curcumin.

The DPPH free radical method is an antioxidant assay based on electron-transfer that produces a violet solution in ethanol. DPPH is a free radical that is stable at room temperature and is reduced in the presence of an antioxidant molecule to give rise to a yellow colored product, diphenylpicryl hydrazine, in ethanol solution. DPPH free radical scavenging is an accepted mechanism for screening the antioxidant activity. The method is widely used due to relatively short time required for the analysis. The free radical scavenging ability of the curcumin, tetrahydrocurcumin, and tetrahydrocurcumin-Zn-curcumin was tested by DPPH radical scavenging assay as per the manufacturer's instruction (Dojindo Molecular Technologies, Inc., Kumamoto, Japan).

Briefly, a solution of 10 mL DPPH in ethanol was prepared, and 100 μl of this solution was mixed with 20 μl of the curcumin, tetrahydrocurcumin, or tetrahydrocurcumin-Zn-curcumin in ethanol at different concentrations (0.125-0.50 mg/mL). The reaction mixture was mixed thoroughly and left in the dark at RT for 30 min. The absorbance of the mixture was measured spectrophotometrically at 517 nm. Trolox was used as reference. Percentage DPPH radical scavenging activity was calculated by the following equation:

$$DPPH \text{ radical scavenging activity (\%)} = (Acs - As)/Acs \times 100$$

Acs: Blank 1—Blank 2

As: Absorbance of samples—Blank 2

Then % of inhibition was plotted against concentration.

Figure 16:
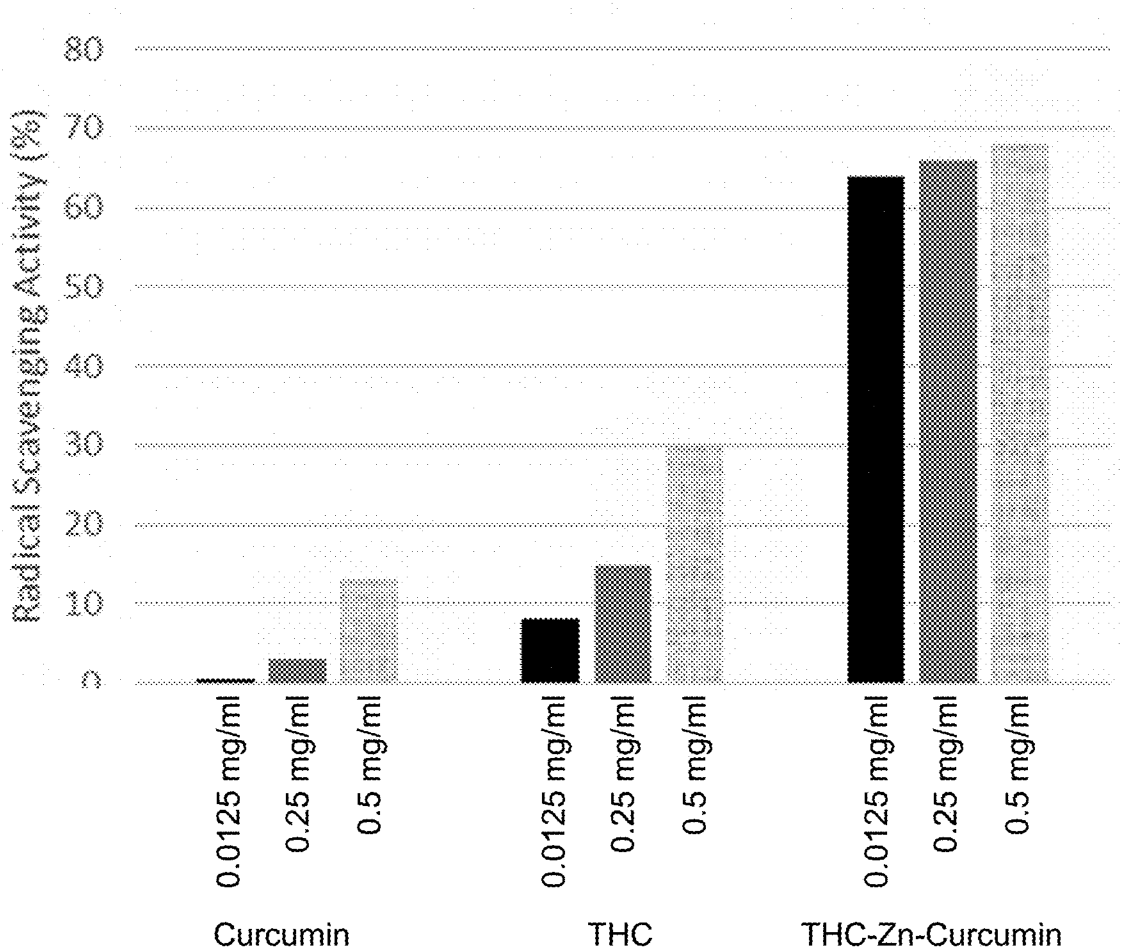
FIG. 16. Antioxidant activity of curcumin (0.125 mg/ml, 0.25, mg/ml, 0.5 mg/ml), tetrahydrocurcumin (THC) (0.125 mg/ml, 0.25, mg/ml, 0.5 mg/ml), and tetrahydrocurcumin (THC)—Zn-curcumin (0.125 mg/ml, 0.25, mg/ml, 0.5 mg/ml) as determined by DPPH (2,2-diphenyl-1-picryl-hydrazyl-hydrate) antioxidant assay.
Figure 17A:
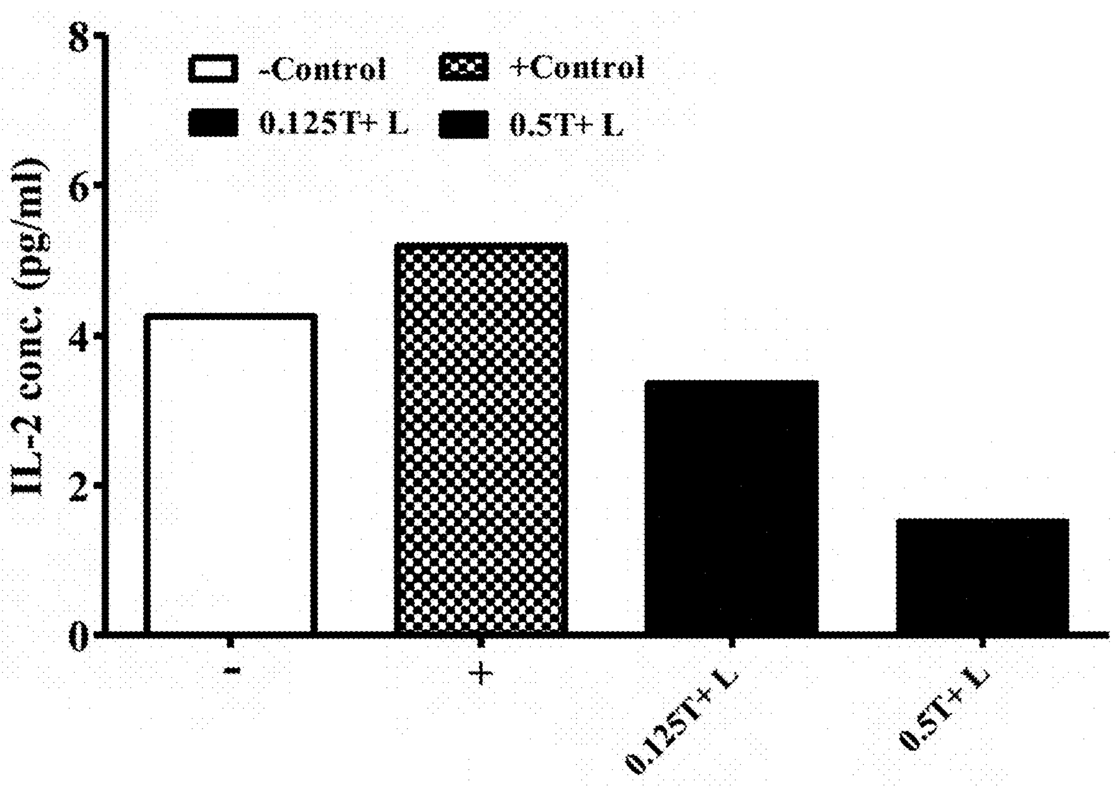
FIGS. 17A-17I. Release of indicated cytokines from MDCK cells not stimulated with lipopolysaccharide (LPS) (−); stimulated with LPS (8 μg/ml) in the absence of tetrahydrocurcumin-Zn-curcumin (+); stimulated with LPS (8 μg/ml) in the presence of 0.125 mg/ml tetrahydrocurcumin-Zn-curcumin (0.125 T+L), 0.25 mg/ml tetrahydrocurcumin-Zn-curcumin (0.25 T+L), 0.5 mg/ml tetrahydrocurcumin-Zn-curcumin (0.5 T+L), or 1 mg/ml tetrahydrocurcumin-Zn-curcumin (1 T+L); or treated with 0.125 mg/ml tetrahydrocurcumin-Zn-curcumin (0.125 T), 0.25 mg/ml tetrahydrocurcumin-Zn-curcumin (0.25 T), or 0.5 mg/ml tetrahydrocurcumin-Zn-curcumin (0.5 T) without stimulation with LPS, as indicated.
Figure 17B:
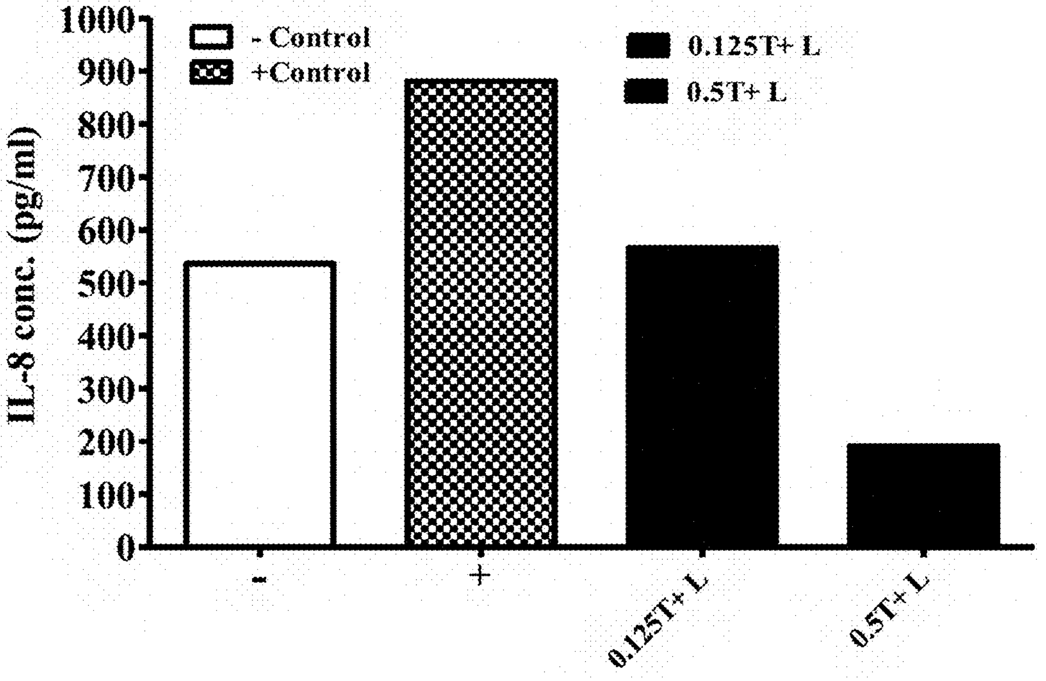
Figure 17C:
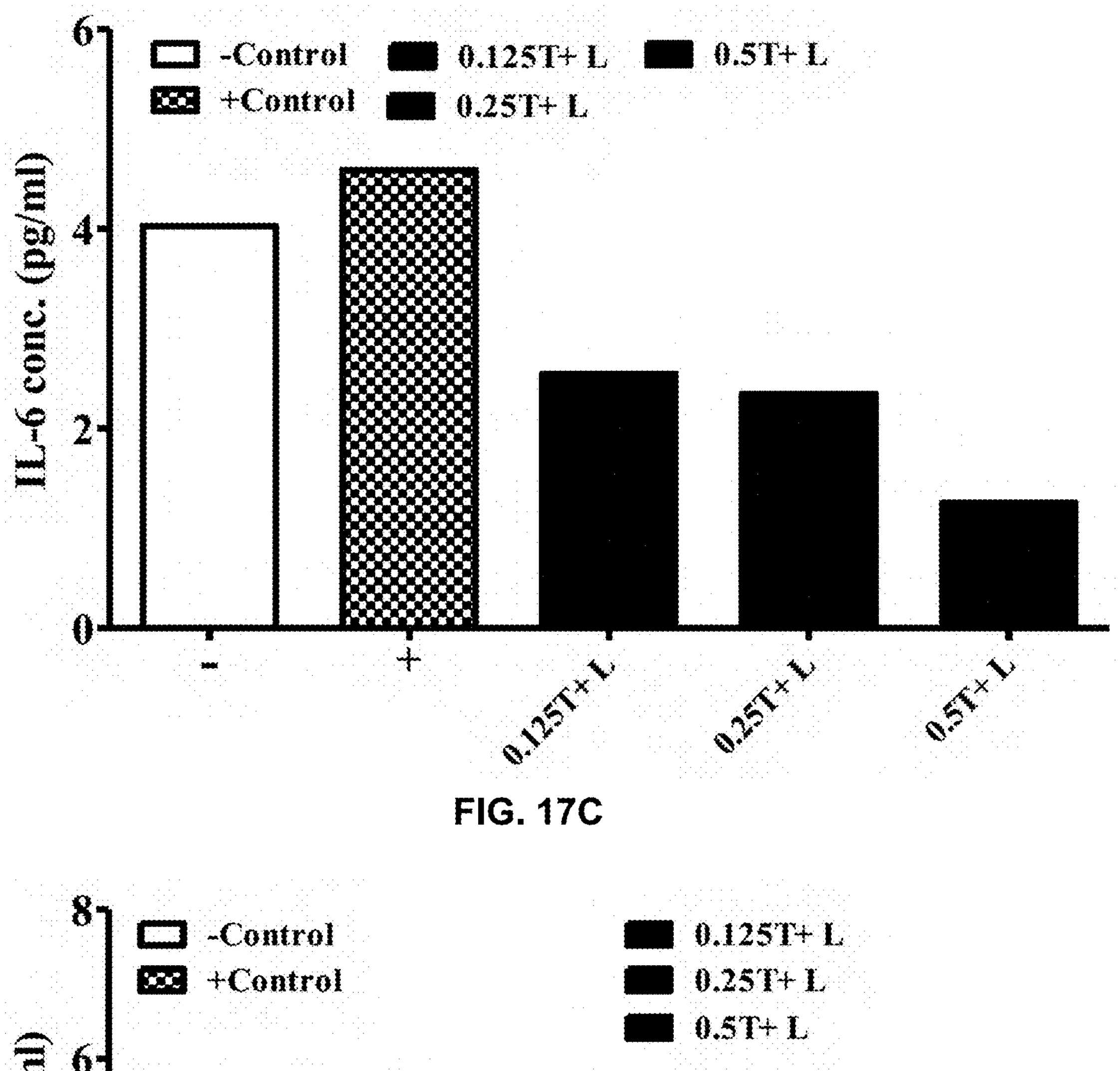
Figure 17D:
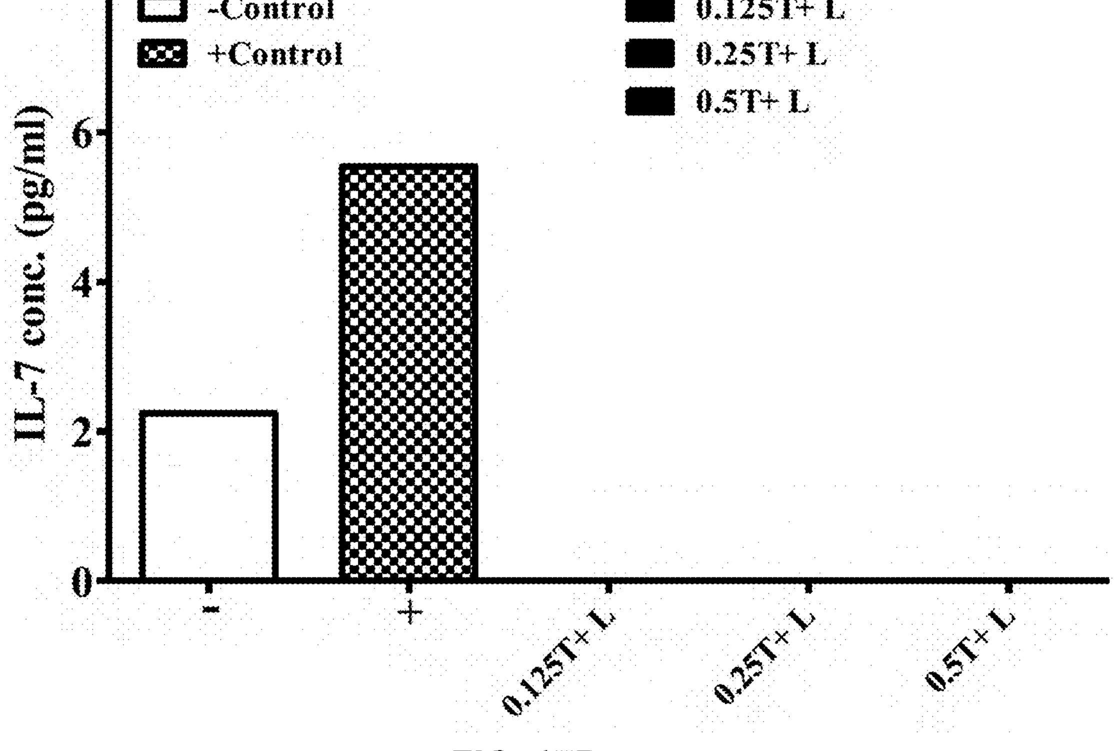
Figure 17E:
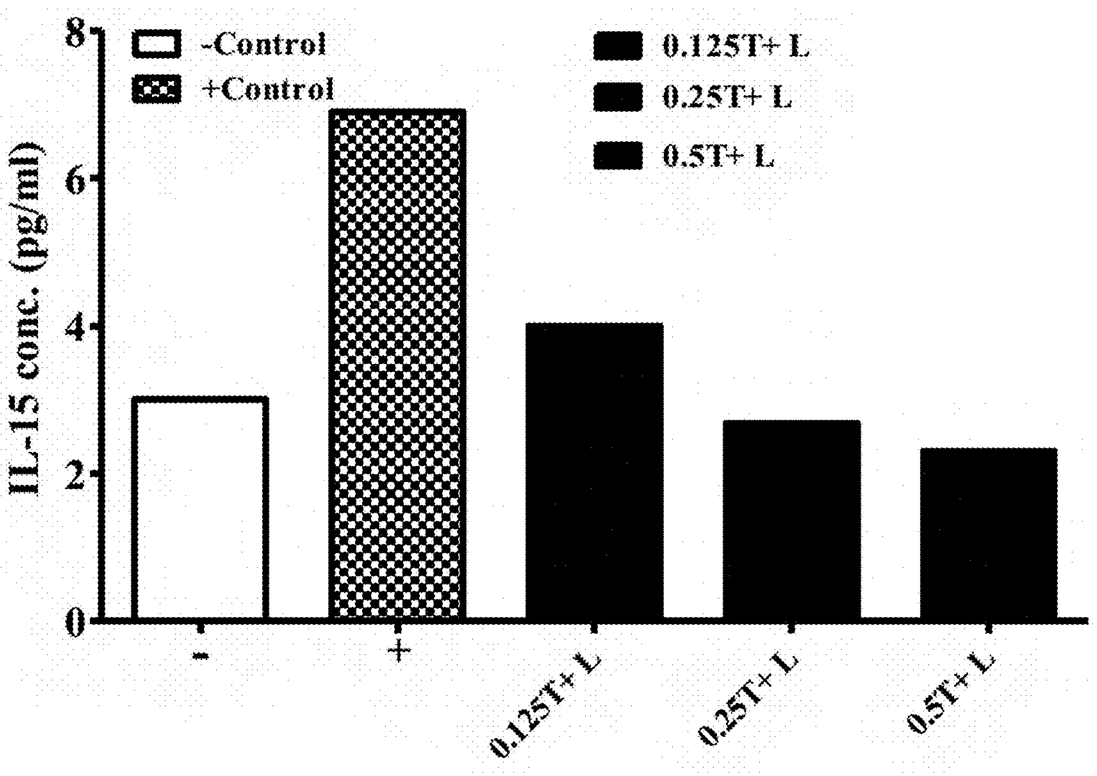
Figure 17F:
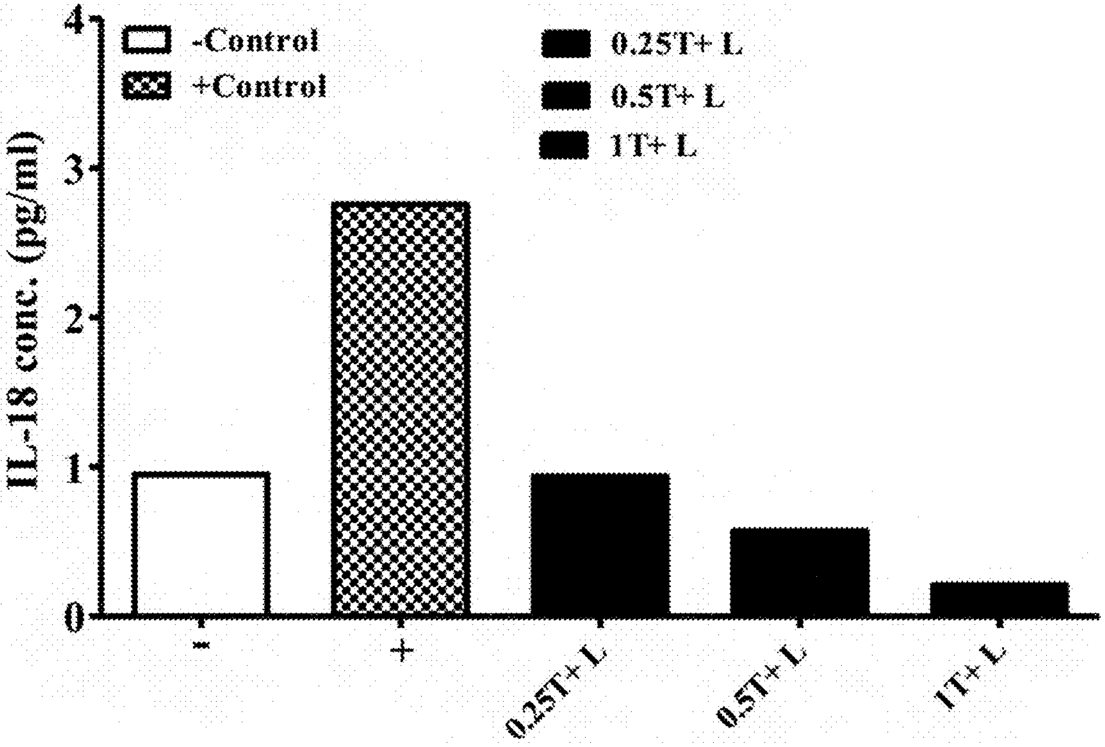
Figure 17G:
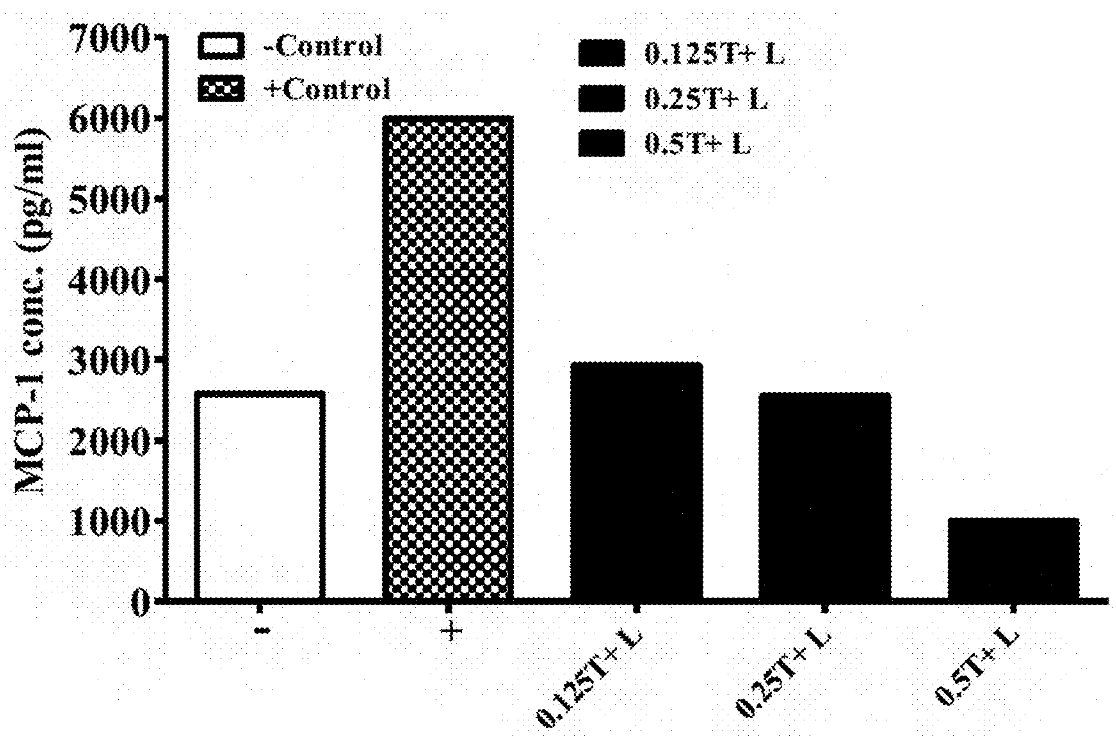
Figure 17H:
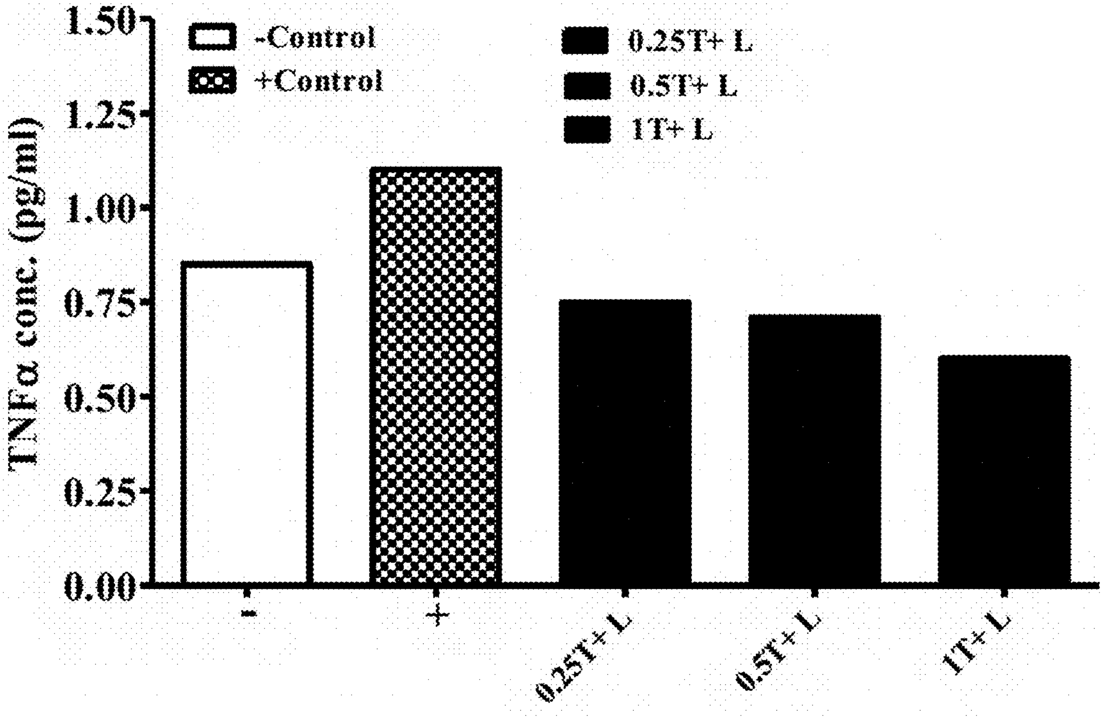
Figure 17I:
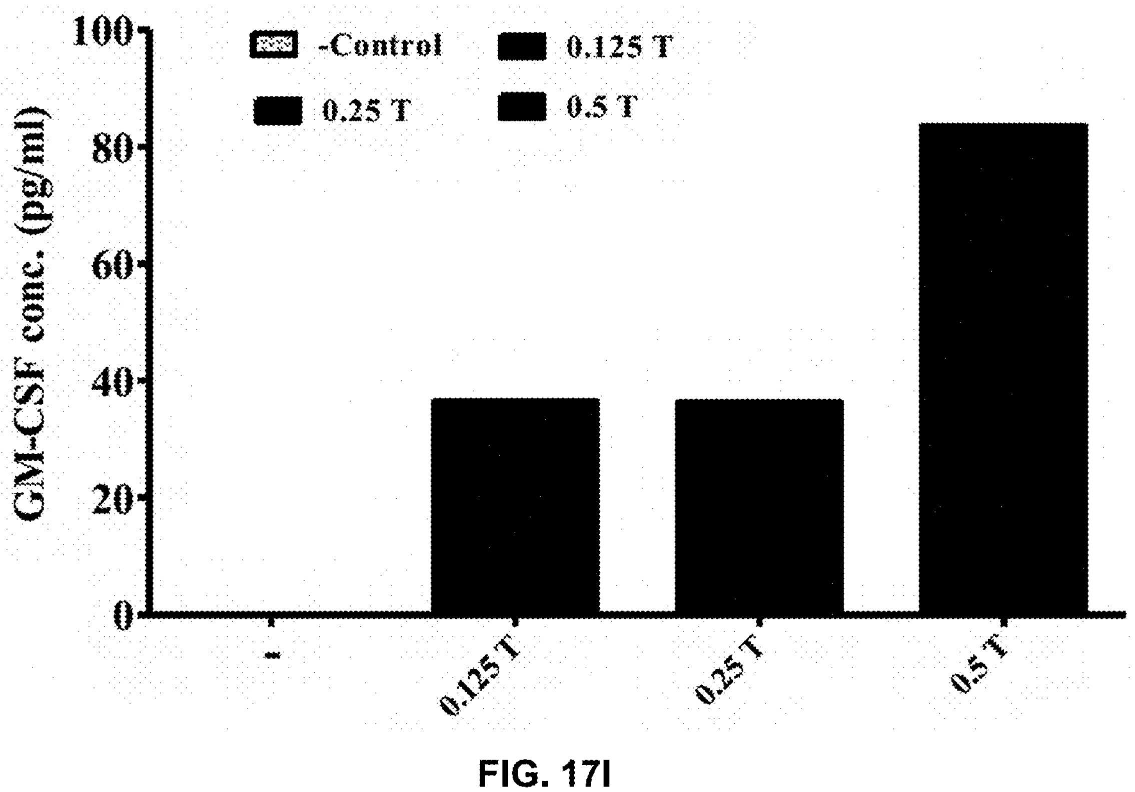

All compounds (curcumin, tetrahydrocurcumin, and tetrahydrocurcumin-Zn-curcumin) exhibited antioxidant activity by scavenging free radicals (FIG. 16) in a dose-dependent manner. Curcumin alone had lowest antioxidant activity among them. Tetrahydrocurcumin exerted a higher antioxidant activity than curcumin but less than the tetrahydrocurcumin-Zn-curcumin. The tetrahydrocurcumin-Zn-curcumin showed the highest level of antioxidant activity as compared to the curcumin or tetrahydrocurcumin. An unexpectant synergistic antioxidant activity of the invention occurred as the amount of antioxidant activity of the tetrahydrocurcumin-Zn-curcumin is much greater than a simple additive effect of the starting curcumin with the starting tetrahydrocurcumin. This unexpected synergistic action can be observed at all doses, but especially with the smallest dose (0.125 mg/ml) in the assay. These results indicate the excellent efficacy of the tetrahydrocurcumin-Zn-curcumin of the invention for vastly improved antioxidant activity over the starting materials of curcumin or tetrahydrocurcumin alone, and at relatively low concentrations.

Example 15

A tetrahydrocurcumin-Zn-curcumin complex of the invention was examined for its ability to influence cytokine release in a cell culture system. Cytokine release leads to systemic inflammatory syndromes involving elevated levels of circulating cytokines and immune-cell hyperactivation. The cytokine release can be triggered by various stresses, viral pathogens like Covid-19, cancers, autoimmune conditions, and monogenic disorders. In cell culture systems, lipopolysaccharide (LPS) is commonly used as stressor to induce cytokine release.

MDCK cells were cultured in a DMEM media supplemented with FBS and antibiotic and were maintained in a humidified atmosphere of 5% $CO_2$ and 95% humidity. Almost 70% confluent cells were treated with different concentrations of tetrahydrocurcumin-Zn-curcumin, curcumin, or tetrahydrocurcumin (0.125, 0.25, 0.5, or 1 mg/ml) in plates containing 3 mL of DMEM. The tetrahydrocurcumin-Zn-curcumin was made as described in Example 9. The curcumin controls and tetrahydrocurcumin controls were from the same starting material used to make the tetrahydrocurcumin-Zn-curcumin. After 2 hours, cells were treated with LPS (8 μg/ml) and incubated for 24 hours. Media were harvested and cytokines were measured using Canine Cytokine Array/Chemokine Array 13-Plex (CD13) at a commercial laboratory (Eve Technologies, Calgary, CA).

FIGS. 17A-17I show lipopolysaccharide (LPS)-stimulated cytokine release in the absence or presence of tetrahydrocurcumin-Zn-curcumin (data were analyzed using GraphPad Prism). LPS stimulated cytokine release over the baseline levels in all cases, except for GM-CSF where the baseline level was zero to begin with. Tetrahydrocurcumin-Zn-curcumin consistently reduced the LPS-stimulated cytokine levels to below baseline levels in a dose-dependent manner. However, in the case of GM-CSF, tetrahydrocurcumin-Zn-curcumin stimulated the release of this particular cytokine.

Cytokines are a diverse group of small proteins that are secreted by cells for the purpose of intercellular signaling, and many, but not all, are associated with pro-inflammatory reactions in the body. Reducing cytokine release from stressed cells or enhancing certain cytokines is important for maintaining the overall health of a human or animal.

IL-2 promotes inflammatory responses and functions to stimulate T-cell growth in asthma, atopic dermatitis, auto immune diseases, cancer and inflammatory bowel disease. The reduction in IL-2 resulting from administration with the tetrahydrocurcumin-Zn-curcumin of the invention would be beneficial, for example, to overall health to an individual with these conditions.

IL-8 plays a pro-inflammatory role as a chemoattractant recruitment of neutrophils. *Babesia* parasite infection in dogs causes increased level of IL-8. The reduction in IL-8 resulting from administration of the tetrahydrocurcumin-Zn-curcumin of the invention would be beneficial, for example, to animals with this parasite infection.

IL-6 is associated with pro-inflammatory responses and responsible for many inflammatory diseases in both humans and animals. In synovial fluid of dogs with cranial cruciate ligament rupture have high level of IL-6 that may results in arthritic symptoms. IL-6 may be involved in the pathogenesis of tubule-glomeruli injury and subclinical ehrlichiosis may lead in chronic kidney disease in dogs. The reduction of IL-6 resulting from administration of the tetrahydrocurcumin-Zn-curcumin of the invention would be beneficial, for example, to both humans and animals suffering from arthritis or other diseases.

IL-7 causes cartilage matrix degradation that may results in joint destruction. High expression of IL-7 causes bone destruction in dogs. IL-7 is overexpressed during viral infection in dogs. The reduction of IL-7 resulting from administration of the tetrahydrocurcumin-Zn-curcumin of the invention would be beneficial, for example, to both humans and animals suffering from arthritis or other diseases.

IL-15 is a pro-inflammatory cytokine that is expressed in several inflammatory disorders, including rheumatoid arthritis, psoriasis, and pulmonary inflammatory diseases. IL-15 and IL-18 are elevated in pyometra disease in dogs. Pyometra is caused by bacterial infection of the uterus and can result in systemic inflammatory response syndrome. The reduction of IL-15 resulting from administration of the tetrahydrocurcumin-Zn-curcumin of the invention would be beneficial, for example, to both humans and animals with these or similar health conditions.

IL-18 has been implicated in several autoimmune diseases, myocardial function, metabolic syndromes, psoriasis, inflammatory bowel disease, hemophagocytic syndromes, macrophage activation syndrome, sepsis, mental cognition issues, and acute kidney injury. IL-18 is highly expressed in dogs with metaphyseal osteopathy (an inflammatory bone disease). the reduction of IL-18 resulting from administration of the tetrahydrocurcumin-Zn-curcumin of the invention would be beneficial, for example, to both humans and animals with these health conditions.

Monocyte chemoattractant protein-1 (MCP-1) is one of the key chemokines that regulate migration and infiltration of monocytes/macrophages to produce inflammation. *Babesia* infection in dogs causes increased level of MCP-1 and further inflammation. The reduction of MCP-1 resulting from administration of the tetrahydrocurcumin-Zn-curcumin of the invention would be beneficial, for example, to both humans and animals with these health conditions.

TNF-α is responsible for range of inflammatory conditions, including rheumatoid arthritis, ankylosing spondylitis, inflammatory bowel disease and psoriasis. TNF-α is noticeably up-regulated in dogs with visceral leishmaniasis disease and chronic kidney disease, and thus considered as a key factor for the initiation, maintenance, and persistence of inflammation. A reduction of TNF-α resulting from administration of the tetrahydrocurcumin-Zn-curcumin of the invention would be beneficial, for example, to both humans and animals with these health conditions Granulocyte-macrophage colony stimulating factor (GM-CSF) stimulates stem cells to produce granulocytes (neutrophils, eosinophils, and basophils) and monocytes. GM-CSF improves intestinal barrier integrity by augmenting innate immune responses. Acutely increased GM-CSF levels resulting from administration of the tetrahydrocurcumin-Zn-curcumin of the invention would be beneficial, for example, for immunity and improving health in humans and animals.

Collectively, these examples and results show the efficacy of the tetrahydrocurcumin-Zn-curcumin of the invention for reducing pro-inflammatory cytokines or augmenting levels of beneficial cytokines. The tetrahydrocurcuminoid-metal complexes can be administered to animals to increase animal health, reduce stress, reduce oxidative stress, maintain health, improve health, improve immunity, improve vaccination efficacy, increase feed conversion rate, and/or decrease pro-inflammatory cytokine levels in an animal.

Example 16

0.25 moles of tetrahydrocurcumin and 0.75 moles of curcumin were mixed together to create 1 mole of ligand as a dry powder and placed in a beaker. One mole of zinc chloride was added to the beaker to give a 1:1 molar ratio of ligand:metal and mixed to form a dry powder mixture of tetrahydrocurcumin, curcumin, and zinc chloride.

REFERENCES

Aggarwal B. B., Deb L. and Prasad S. Curcumin Differs from Tetrahydrocurcumin for Molecular Targets, Signaling Pathways and Cellular Responses. Molecules 2015, 20, 185-205.

Dai J, Gu L, Su Y, Wang Q, Zhao Y, Chen X, Deng H, Li W, Wang G, Li K. Inhibition of curcumin on influenza A virus infection and influenzal pneumonia via oxidative stress, TLR2/4, p38/JNK MAPK and NF-κB pathways. Int Immunopharmacol. 2018 January; 54:177-187. doi: 10.1016/j.intimp.2017.11.009. Epub 2017 Nov. 15.

Fosmire G J. Zinc toxicity. Am J Clin Nutr. 1990 February; 51(2):225-7.

Hieu T. Q. and Thao D. T. T. Enhancing the Solubility of Curcumin Metal Complexes and Investigating Some of Their Biological Activities. Journal of Chemistry Volume 2019, Article ID 8082195, 8 pages https://doi.org/10.1155/2019/8082195

Ostrowski W., Uniecikowska L., Hoffmann M., and Franski R. Demethoxycurcumin-Metal Complexes: Fragmentation and Comparison with Curcumin-Metal Complexes, as Studied by ESI-MS/MS Journal of Spectroscopy. Volume 2013, Article ID 749641, 8 pages http://dx.doi.org/10.1155/2013/749641

McCarty, Mark F, and James J DiNicolantonio. "Nutraceuticals have potential for boosting the type 1 interferon response to RNA viruses including influenza and coronavirus." Progress in cardiovascular diseases, S0033-0620 (20)30037-2. 12 Feb. 2020, doi:10.1016/j.pcad.2020.02.007

Shoba G, Joy D, Joseph T, Majeed M, Rajendran R, Srinivas P S. Influence of piperine on the pharmacokinetics of curcumin in animals and human volunteers. Planta Med. 1998 May; 64(4):353-6.

What is claimed is:

1. A method of decreasing feed conversion ratio in a production animal, the method comprising orally administering a composition in an amount and for a time effective to decrease the feed conversion ratio in the production animal, wherein the composition comprises an effective amount of a tetrahydrocurcumin-zinc-curcumin complex having the following structure:

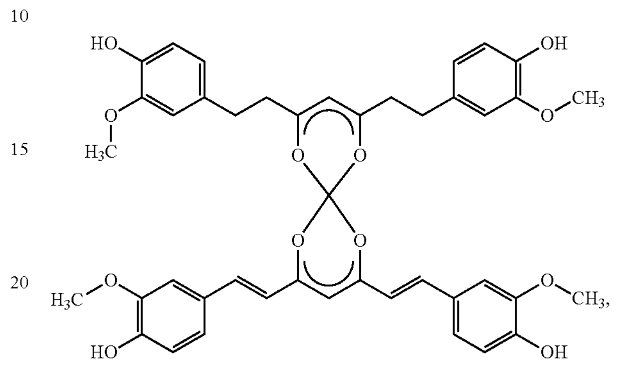

or a salt thereof.

2. The method of claim 1, wherein the composition is administered to the production animal in an amount of at least 0.1% w/w of the total feed consumed by the production animal.

3. The method of claim 1, wherein the composition is administered to the production animal in an amount of at least 0.5% w/w of the total feed consumed by the production animal.

4. The method of claim 1, wherein the composition is administered to the production animal in an amount of at least 1% w/w of the total feed consumed by the production animal.

5. The method of claim 1, wherein the composition is administered for a period of at least three weeks.

6. The method of claim 1, wherein the composition is administered to the production animal in an amount of at least 0.1% w/w of the total feed consumed by the production animal for a period of at least three weeks.

7. The method of claim 1, wherein the composition is administered to the production animal in an amount of at least 0.5% w/w of the total feed consumed by the production animal for a period of at least three weeks.

8. The method of claim 1, wherein the composition is administered to the production animal in an amount of at least 1% w/w of the total feed consumed by the production animal for a period of at least three weeks.

9. The method of claim 1, wherein the production animal is a mammal.

10. The method of claim 1, wherein the production animal is an avine, a bovine, an ovine, a porcine, or a caprine.

11. The method of claim 1, wherein the composition is administered in an amount effective to decrease serum levels of at least one of IL-1-beta and IL-6 in the production animal.

12. The method of claim 11, wherein the composition is administered to the production animal in an amount of at least 0.1% w/w of the total feed consumed by the production animal.

13. The method of claim 11, wherein the composition is administered to the production animal in an amount of at least 0.5% w/w of the total feed consumed by the production animal.

14. The method of claim 11, wherein the composition is administered to the production animal in an amount of at least 1% w/w of the total feed consumed by the production animal.

15. The method of claim 11, wherein the composition is administered for a period of at least three weeks.

16. The method of claim 11, wherein the composition is administered to the production animal in an amount of at least 0.1% w/w of the total feed consumed by the production production animal for a period of at least three weeks.

17. The method of claim 11, wherein the composition is administered to the production animal in an amount of at least 0.5% w/w of the total feed consumed by the production animal for a period of at least three weeks.

18. The method of claim 11, wherein the composition is administered to the production animal in an amount of at least 1% w/w of the total feed consumed by the production animal for a period of at least three weeks.

* * * * *